(12) United States Patent
Surleraux et al.

(10) Patent No.: US 8,143,421 B2
(45) Date of Patent: Mar. 27, 2012

(54) BROADSPECTRUM SUBSTITUTED BENZIMIDAZOLE SULFONAMIDE HIV PROTEASE INHIBITORS

(75) Inventors: Dominique Louis Nestor Ghislain Surleraux, Machelen (BE); Piet Tom Bert Paul Wigerinck, Terhagen (BE); Marieke Christiane Johanna Diepenbeek Voets, Diepenbeek (BE); Sandrine Marie Helene Vendeville, Brussels (BE); Herman Augustinus De Kock, Arendonk (BE); Bernhard Joanna Bernard Vergouwen, Maaseik (BE)

(73) Assignee: Tibotec Pharmaceuticals Ltd., Little Island (IE)

( * ) Notice: Subject to any disclaimer, the term of this patent is extended or adjusted under 35 U.S.C. 154(b) by 281 days.

(21) Appl. No.: 12/430,547

(22) Filed: Apr. 27, 2009

(65) Prior Publication Data
US 2009/0203743 A1  Aug. 13, 2009

Related U.S. Application Data

(63) Continuation of application No. 10/508,561, filed as application No. PCT/EP03/50057 on Mar. 12, 2003, now abandoned.

(30) Foreign Application Priority Data

Mar. 12, 2002 (EP) .................................... 02075999

(51) Int. Cl.
*A61K 31/4184* (2006.01)
*C07D 405/12* (2006.01)

(52) U.S. Cl. ..................... 548/305.1; 514/394; 514/338; 514/365; 546/273.4; 548/181

(58) Field of Classification Search ................ 548/305.1
See application file for complete search history.

(56) References Cited

U.S. PATENT DOCUMENTS 6,172,101 B1  1/2001 Getman et al.

FOREIGN PATENT DOCUMENTS

| EP | 499299 A2 | 8/1992 |
|---|---|---|
| EP | 499299 A3 | 8/1992 |
| EP | 721331 A1 | 12/1999 |
| EP | 0499299 B1 | 8/2000 |
| EP | 721331 B1 | 12/2001 |
| WO | WO 94/05263 A1 | 3/1994 |
| WO | WO 95/06030 A1 | 3/1995 |
| WO | WO 96/22287 A1 | 7/1996 |
| WO | WO 96/28418 A1 | 9/1996 |
| WO | WO 96/28463 A1 | 9/1996 |
| WO | WO 96/28464 A1 | 9/1996 |
| WO | WO 96/28465 A1 | 9/1996 |
| WO | 97/18205 A1 | 5/1997 |
| WO | WO 97/18205 A1 | 5/1997 |
| WO | WO 97/44014 A1 | 11/1997 |
| WO | WO 98/42318 A1 | 10/1998 |
| WO | 99/33792 A3 | 7/1999 |
| WO | 99/33793 A3 | 7/1999 |
| WO | WO 99/33792 A2 | 7/1999 |
| WO | WO 99/33793 A2 | 7/1999 |
| WO | WO 99/33795 A1 | 7/1999 |
| WO | WO 99/33815 A1 | 7/1999 |
| WO | WO 99/59989 A1 | 11/1999 |
| WO | 99/65870 A3 | 12/1999 |

(Continued)

OTHER PUBLICATIONS

Augustijns, P., et al. "Drug Absorption Studies of Prodrug Esters Using the Caco-2 Model: Evaluation of Ester Hydrolysis and Transepithelial Transport", International Journal of Pharmaceutics, vol. 166 pp. 45-53 (1998).

(Continued)

*Primary Examiner* — Laura L. Stockton

(57) ABSTRACT

The present invention concerns the compounds having the formula

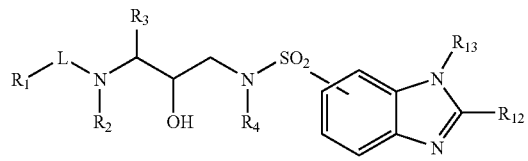

N-oxides, salts, stereoisomeric forms, racemic mixtures, prodrugs, esters and metabolites thereof, wherein $R_1$ and $R_8$ each are H, optionally substituted $C_{1-6}$alkyl, $C_{2-6}$alkenyl, $C_{3-7}$cycloalkyl, aryl, $Het^1$, $Het^2$; $R_1$ may also be a radical of formula $(R_{11a}R_{11b})NC(R_{10a}R_{10b})CR_9$—; t is 0, 1 or 2; $R_2$ is H or $C_{1-6}$alkyl; L is —C(=O)—, —O—C(=O)—, —NR$_8$—C(=O)—, —O—$C_{1-6}$alkanediyl-C(=O)—, —NR$_8$—$C_{1-6}$alkanediyl-C(=O)—, —S(=O)$_2$—, —O—S(=O)$_2$—, —NR$_8$—S(=O)$_2$; $R_3$ is $C_{1-6}$alkyl, aryl, $C_{3-7}$cycloalkyl, $C_{3-7}$cycloalkyl$C_{1-4}$alkyl, or aryl$C_{1-4}$alkyl; $R_4$ is H, $C_{1-4}$alkylOC(=O), carboxyl, aminoC(=O), mono- or di($C_{1-4}$alkyl)aminoC(=O), $C_{3-7}$cycloalkyl, $C_{2-6}$alkenyl, $C_{2-6}$alkynyl or optionally substituted $C_{1-6}$alkyl; A is $C_{1-6}$alkanediyl, —C(=O)—, —C(=S)—, —S(=O)$_2$—, $C_{1-6}$alkanediyl-C(=O)—, $C_{1-6}$alkanediyl-C(=S)— or $C_{1-6}$alkanediyl-S(=O)$_2$—; $R_5$ is H, OH, $C_{1-6}$alkyl, $Het^1C_{1-6}$alkyl, $Het^2C_{1-6}$alkyl, optionally substituted amino-$C_{1-6}$alkyl; $R_6$ is $C_{1-6}$alkylO, $Het^1$, $Het^1O$, $Het^2$, $Het^2O$, aryl, arylO, $C_{1-6}$alkyloxy-carbonylamino or amino; and in case -A- is other than $C_{1-6}$alkanediyl then $R^6$ may also be $C_{1-6}$alkyl, $Het^1C_{1-4}$alkyl, $Het^1OC_{1-4}$alkyl, $Het^2C_{1-4}$alkyl, $Het^2OC_{1-4}$alkyl, aryl$C_{1-4}$alkyl, arylO$C_{1-4}$alkyl or amino$C_{1-4}$alkyl; whereby each of the amino groups in the definition of $R_6$ may optionally be substituted; $R^5$ and -A-$R^6$ taken together with the nitrogen atom to which they are attached may also form $Het^1$ or $Het^{2*}$ $R_{12}$ is H, —NH$_2$, —NR$^5$AR$^6$, —$C_{1-6}$alkyl or alkyl-W—$R_{14}$, wherein said alkyl is optionally substituted with halogen, hydroxy, aryl, heteroaryl, $Het^1$, $Het^2$, or amino wherein said amino is optionally mono- or di-substituted with $C_{1-4}$alkyl and $R_{13}$ is H, $C_{1-6}$-alkyl, optionally substituted by aryl, $Het^1$, $Het^2$, hydroxy, halogen, amino whereby the amino group may be optionally be mono- or di-substituted with $C_{1-4}$alkyl.

5 Claims, No Drawings

FOREIGN PATENT DOCUMENTS

| | | |
|---|---|---|
| WO | 99/67254 A3 | 12/1999 |
| WO | WO 99/65870 A2 | 12/1999 |
| WO | WO 99/67254 A2 | 12/1999 |
| WO | WO 00/76961 A1 | 12/2000 |

OTHER PUBLICATIONS

Freskos, J., et al. "Preparation of bis(sulfonamide Hydroxethylamino Peptide Analogs as Retroviral Protease Inhibitors", Accession No. 1996:572053.

Getman, D., et al. Preparation of Heterocycicarboyl Amino Acid Hydroxyethylamino Sulfonamide retroviral Protesae Inhibitors, Accession No. 2001: 25780.

Hertogs, K., et al. "A Rapid Method for Simultaneous Detection of Phenotypic Resistance to Inhibitors of Protease and Reverse Transcriptase in Recombinant Human Immunodeficiency Virus Type 1 Isolate sfrom Patients Treated With Antiretroviral Drug", Antimocribial Agents and Chemotherapy, pp. 269-276 (1998).

International Search Report dated Jul. 28, 2003 for related International Application No. PCT/EP2003/50057.

Goodman and Gilman, The Pharmacological Basis of Therapeutics, 8$^{th}$ ed, McGraw-Hill, Int. Ed. (1992), "Biotransformation of Drugs", pp. 13-15.

Cross, L.C., et al., "Rules for the Nomenclature of Organic Chemistry", International Union of Pure Applied Chemistry, Pure & Appl. Chem., (1976), vol. 45, pp. 11-30.

Chou and Talalay, "Quantitative Analysis of Dose-Effect Relationships; The Combined Effects of Multiple Drugs or Enzyme Inhibitors", Advances in Enzyme Regulation, (1984), vol. 22, pp. 27-55.

Courtin, V.A., "Syntheses of Sulfonated Derivatives of 2-Fluoroaniline", Helvetica Chimica Acta, (1983), vol. 66, fasc. 1, pp. 68-75.

BROADSPECTRUM SUBSTITUTED BENZIMIDAZOLE SULFONAMIDE HIV PROTEASE INHIBITORS

CROSS REFERENCE TO RELATED APPLICATIONS

This application is a continuation of U.S. application Ser. No. 10/508,561, filed Sep. 10, 2004, now abandoned which in turn is a national stage of PCT Application No. PCT/EP2003/50057, filed Mar. 12, 2003, which application claims priority benefit of EP 02075999.9, filed Mar. 12, 2002, the entire disclosures of which are hereby incorporated in their entirely.

The present invention relates to substituted-benzimidazole sulfonamides, their use as aspartic protease inhibitors, in particular as broadspectrum HIV protease inhibitors, processes for their preparation as well as pharmaceutical compositions and diagnostic kits comprising them. The present invention also concerns combinations of the present substituted benzimidazole sulfonamides with another anti-retroviral agent. It further relates to their use in assays as reference compounds or as reagents.

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

One of the critical pathways in a retroviral life cycle is the processing of polyprotein precursors by aspartic protease. For instance the HIV viral gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

HIV protease inhibitors (PIs) are commonly administered to AIDS patients in combination with other anti-HIV compounds such as, for instance nucleoside reverse transcriptase inhibitors (NRTIs), non-nucleoside reverse transcriptase inhibitors (NNRTIs), fusion inhibitors such as T-20 or other protease inhibitors. Despite the fact that these antiretrovirals are very useful, they have a common limitation, namely, the targeted enzymes in the HIV virus are able to mutate in such a way that the known drugs become less effective, or even ineffective against these mutant HIV viruses. Or, in other words, the HIV virus creates an ever increasing resistance against the available drugs.

Resistance of retroviruses, and in particular the HIV virus, against inhibitors is a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need in the art for new compounds for retrovirus therapy, more particularly for AIDS therapy. The need in the art is particularly acute for compounds that are active not only on wild type HIV virus, but also on the increasingly more common resistant HIV viruses.

Known antiretrovirals, often administered in a combination therapy regimen, will eventually cause resistance as stated above. This often may force the physician to boost the plasma levels of the active drugs in order for said antiretrovirals to regain effectivity against the mutated HIV viruses. The consequence of which is a highly undesirable increase in pill burden. Boosting plasma levels may also lead to an increased risk of non-compliance with the prescribed therapy. Thus, it is not only important to have compounds showing activity for a wide range of HIV mutants, it is also important that there is little or no variance in the ratio between activity against mutant HIV virus and activity against wild type HIV virus (also defined as fold resistance or FR) over a broad range of mutant HIV strains. As such, a patient may remain on the same combination therapy regimen for a longer period of time since the chance that a mutant HIV virus will be sensitive to the active ingredients will be increased.

Finding compounds with a high potency on the wild type and on a wide variety of mutants is also of importance since the pill burden can be reduced if therapeutic levels are kept to a minimum. One way of reducing this pill burden is finding anti-HIV compounds with good bioavailability, i.e. a favourable pharmacokinetic and metabolic profile, such that the daily dose can be minimized and consequently also the number of pills to be taken.

Another important characteristic of a good anti-HIV compound is that plasma protein binding of the inhibitor has minimal or even no effect on its potency.

Thus, there is a high medical need for protease inhibitors that are able to combat a broad spectrum of mutants of the HIV virus with little variance in fold resistance, have a good bioavailability and experience little or no effect on their potency due to plasma protein binding.

Up until now, several protease inhibitors are on the market or are being developed. One particular core structure (depicted below) has been disclosed in a number of references, such as, WO 95/06030, WO 96/22287, WO 96/28418, WO 96/28463, WO 96/28464, WO 96/28465, WO 99/65870, WO 99/67254, WO 00/76961 and WO 97/18205. The compounds disclosed therein are described as retroviral protease inhibitors.

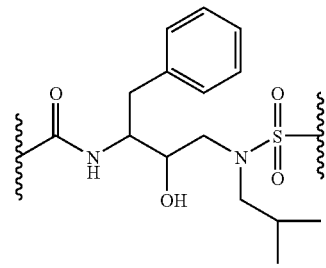

WO 99/67254 discloses 4-substituted-phenyl sulfonamides capable of inhibiting multi-drug resistant retroviral proteases.

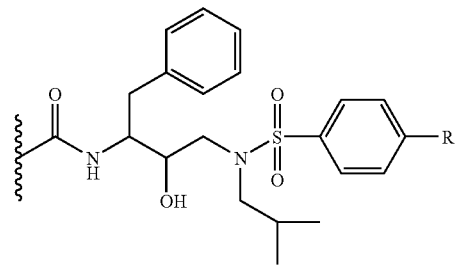

Surprisingly, the substituted-benzimidazole sulfonamides of the present invention are found to have a favourable pharmacological and pharmacokinetic profile. Not only are they active against wild-type HIV virus, but they also show a broad spectrum activity against various mutant HIV viruses exhibiting resistance against known protease inhibitors.

The present invention concerns 2-(substituted-amino)-benzimidazole protease inhibitors, having the formula

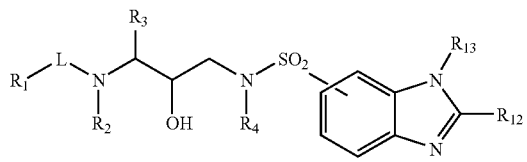

and N-oxides, salts, stereoisomeric forms, racemic mixtures, prodrugs, esters and metabolites thereof, wherein $R_1$ is hydrogen, $C_{1-6}$alkyl, $C_{2-6}$ alkenyl, aryl$C_{1-6}$alkyl, aryl $C_{2-6}$alkenyl, $C_{3-7}$cycloalkyl, $C_{3-7}$cycloalkyl$C_{1-6}$alkyl, aryl, Het$^1$, Het$^1C_{1-6}$alkyl, Het$^2$, Het$^2C_{1-6}$alkyl, $R_1$ may also be a radical of formula

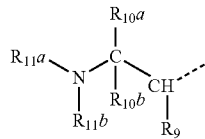

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, Het$^1$, Het$^2$, $C_{3-7}$cycloalkyl, $C_{1-4}$alkyloxycarbonyl, carboxyl, aminocarbonyl, mono- or di($C_{1-4}$alkyl) aminocarbonyl, aminosulfonyl, $C_{1-4}$alkylS(O)$_t$, hydroxy, cyano, halogen or optionally mono- or disubstituted amino where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl; whereby $R_9$, $R_{10a}$ and the carbon atoms to which they are attached optionally form a $C_{3-7}$cycloalkyl radical;

$R_{11a}$ is hydrogen, $C_{2-6}$alkenyl, $C_{2-6}$alkynyl, $C_{3-7}$cycloalkyl, aryl, optionally mono- or disubstituted aminocarbonyl, optionally mono- or disubstituted amino $C_{1-4}$alkylcarbonyloxy, $C_{1-4}$alkyloxycarbonyl, aryloxycarbonyl, Het$^1$oxycarbonyl, Het$^2$oxycarbonyl, aryloxycarbonyl$C_{1-4}$alkyl, aryl$C_{1-4}$alkyloxycarbonyl, $C_{1-4}$alkylcarbonyl, $C_{3-7}$cycloalkylcarbonyl, $C_{3-7}$cycloalkyl$C_{1-4}$alkyloxycarbonyl, $C_{3-7}$cycloalkylcarbonyloxy, carboxyl$C_{1-4}$alkylcarbonyloxy, $C_{1-4}$alkylcarbonyloxy, aryl$C_{1-4}$alkyl-carbonyloxy, arylcarbonyloxy, aryloxycarbonyloxy, Het$^1$carbonyl, Het$^1$carbonyloxy, Het$^1C_{1-4}$alkyloxycarbonyl, Het$^2$ carbonyloxy, Het$^2C_{1-4}$alkylcarbonyloxy, Het$^2C_{1-4}$alkyloxycarbonyloxy or $C_{1-4}$alkyl optionally substituted with aryl, aryloxy, Het$^2$ or hydroxy; wherein the optional substituents on the amino groups are each independently selected from $C_{1-4}$alkyl, aryl, aryl$C_{1-4}$alkyl, $C_{3-7}$cycloalkyl, $C_{3-7}$ cycloalkyl-$C_{1-4}$ alkyl, Het$^1$, Het$^2$, Het$^1C_{1-4}$alkyl and Het$^2C_{1-4}$alkyl; whereby $R_{11a}$ may be optionally linked to the remainder of the molecule via a sulfonyl group;

$R_{11b}$ is hydrogen, $C_{3-7}$cycloalkyl, $C_{2-6}$alkenyl, $C_{2-6}$alkynyl, aryl, Het$^1$, Het$^2$ or $C_{1-4}$alkyl optionally substituted with halogen, hydroxy, $C_{1-4}$alkylS(=O)$_t$, aryl, $C_{3-7}$cycloalkyl, Het$^1$, Het$^2$, optionally mono- or disubstituted amino where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

Each t independently is zero, 1 or 2;

$R_2$ is hydrogen or $C_{1-6}$alkyl;

L is —C(=O)—, —O—C(=O)—, —NR$_8$—C(=O)—, —O—$C_{1-6}$alkanediyl-C(=O)—, —NR$_8$—$C_{1-6}$alkanediyl-C(=O)—, —S(=O)$_2$—, —O—S(=O)$_2$—, —NR$_8$—S(=O)$_2$, —NR$_8$—$C_{1-6}$ alkanediyl-S(=O)$_2$, whereby either the C(=O) group or the S(=O)$_2$ group is attached to the NR$_2$ moiety; whereby the $C_{1-6}$alkanediyl moiety is optionally substituted with hydroxy, aryl, Het$^1$ or Het$^2$;

$R_3$ is $C_{1-6}$alkyl, aryl, $C_{3-7}$cycloalkyl, $C_{3-7}$cycloalkyl$C_{1-4}$ alkyl, or aryl$C_{1-4}$alkyl optionally substituted with $C_{1-4}$alkyl, halogen, nitro, cyano, polyhalo$C_{1-4}$alkyl, hydroxy, $C_{1-4}$alkyloxy, mercapto or $C_{1-4}$alkylthio;

$R_4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, Het$^1$, Het$^2$, $C_{3-7}$ cycloalkyl, $C_{1-4}$alkyloxycarbonyl, carboxyl, aminocarbonyl, mono- or di($C_{1-4}$ alkyl)aminocarbonyl, aminosulfonyl, $C_{1-4}$alkylS(=O)$_t$, hydroxy, cyano, halogen or optionally mono- or disubstituted amino where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$ alkyl; or $R_4$ may also be —X—$R_7$ wherein X is —O— or —N($R_7$)—Y—;

Y is —C(=O)—, —S(=O)$_2$—, —O—C(=O)—, —NR$_8$—C(=O)—, —C(=O)—C(=O)—, —O—S(=O)$_2$— or —NR$_8$—S(=O)$_2$—;

$R_5$ is hydrogen, hydroxy, $C_{1-6}$alkyl, Het$^1C_{1-6}$alkyl, Het$^2C_{1-6}$ alkyl, amino$C_{1-6}$alkyl whereby the amino group may optionally be mono- or di-substituted with $C_{1-4}$alkyl;

$R_6$ is hydrogen, $C_{1-6}$alkyloxy, Het$^1$, Het$^1$oxy, Het$^2$, Het$^2$oxy, aryl, aryloxy, aryloxy-$C_{1-4}$alkyl, $C_{1-4}$alkyloxyaryl, $C_{1-4}$ alkyloxyHet$^1$, $C_{1-4}$ alkyloxyHet$^2$, $C_{1-4}$alkyloxy-carbonylamino, amino$C_{1-4}$alkylamino, amino or amino$C_{1-4}$alkyloxy and in case A is other than $C_{1-6}$alkanediyl, then $R_6$ may also be $C_{1-6}$alkyl, Het$^1C_{1-4}$alkyl, Het$^1$oxy$C_{1-4}$alkyl, Het$^2C_{1-4}$alkyl, Het$^2$oxy$C_{1-4}$alkyl, aryl$C_{1-4}$alkyl, aryloxy$C_{1-4}$alkyl or amino$C_{1-4}$alkyl; whereby each amino group may optionally be mono- or where possible disubstituted with $C_{1-4}$alkyl;

$R_5$ and -A-$R_6$ taken together with the nitrogen atom to which they are attached may also form Het$^1$ or Het$^2$;

$R_7$ is hydrogen, aryl, $C_{3-7}$cycloalkyl, Het$^1$, Het$^2$, $C_{2-6}$alkenyl, $C_{2-6}$alkynyl or $C_{1-6}$alkyl optionally substituted with aryl, Het$^1$, Het$^2$, $C_{3-7}$cycloalkyl, $C_{1-4}$ alkyloxycarbonyl, carboxyl, aminocarbonyl, mono- or di($C_{1-4}$alkyl)aminocarbonyl, aminosulfonyl, $C_{1-4}$alkylS(=O)$_t$, hydroxy, cyano, halogen or amino optionally mono- or disubstituted where the substituents are selected from $C_{1-4}$alkyl, aryl, aryl$C_{1-4}$ alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

$R_8$ is hydrogen, $C_{1-6}$alkyl, $C_{2-6}$alkenyl, aryl$C_{1-6}$alkyl, $C_{3-7}$cycloalkyl, $C_{3-7}$cycloalkyl-$C_{1-6}$alkyl, aryl, Het$^1$, Het$^1C_{1-6}$ alkyl, Het$^2$, Het$^2C_{1-6}$alkyl;

$R_{12}$ is hydrogen, —NH$_2$, —$C_{1-6}$alkyl or $C_{1-6}$alkyl-W—$R_{14}$, wherein said $C_{1-6}$alkyl is optionally substituted with halogen, hydroxy, aryl, heteroaryl, Het$^1$, Het$^2$, or amino wherein said amino is optionally mono- or di-substituted with $C_{1-4}$ alkyl; or $R_{12}$ may also be —N($R_5$)(A$R_6$), wherein A is $C_{1-6}$alkanediyl, —C(=O)—, —C(=S)—, —S(=O)$_2$—, $C_{1-6}$alkanediyl-C(=O)—, $C_{1-6}$alkanediyl-C(=S)— or $C_{1-6}$alkanediyl-S(=O)$_2$—; wherein if A is $C_{1-6}$alkanediyl-C(=O)—, $C_{1-6}$alkanediyl-C(=S)— or $C_{1-6}$alkanediyl-S(=O)$_2$—, the N$R_5$ moiety is attached to the $C_{1-6}$alkanediyl moiety;

W is oxy, carbonyl, oxycarbonyl, carbonyloxy, oxycarbonyloxy, amino, aminocarbonyl, carbonylamino or sulphur;

$R_{13}$ is hydrogen, $C_{1-6}$-alkyl, optionally substituted by aryl, Het$^1$, Het$^2$, hydroxy, halogen, amino whereby the amino group may be optionally be mono- or di-substituted with $C_{1-4}$alkyl;

$R_{14}$ is $C_{1-6}$alkyl, aryl, Het$^1$ or Het$^2$.

This invention also includes the quaternization of the nitrogen atoms of the present compounds. A basic nitrogen can be quaternized with any agent known to those of ordinary skill in the art including, for instance, lower alkyl halides, dialkyl sulfates, long chain halides and aralkyl halides.

Whenever the term substituted is used in defining the compounds of formula (I), it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "halo" or "halogen" as a group or part of a group is generic for fluoro, chloro, bromo or iodo.

The term "$C_{1-4}$alkyl" as a group or part of a group defines straight and branched chained saturated hydrocarbon radicals having from 1 to 4 carbon atoms, such as, for example, methyl, ethyl, propyl, butyl and 2-methyl-propyl, the like.

The term "$C_{1-6}$alkyl" as a group or part of a group defines straight and branched chained saturated hydrocarbon radicals having from 1 to 6 carbon atoms such as the groups defined for $C_{1-4}$alkyl and pentyl, hexyl, 2-methylbutyl, 3-methylpentyl and the like.

The term "$C_{1-6}$ alkanediyl" as a group or part of a group defines bivalent straight and branched chained saturated hydrocarbon radicals having from 1 to 6 carbon atoms such as, for example, methylene, ethan-1,2-diyl, propan-1,3-diyl, propan-1,2-diyl, butan-1,4-diyl, pentan-1,5-diyl, hexan-1,6-diyl, 2-methylbutan-1,4-diyl, 3-methylpentan-1,5-diyl and the like.

The term "$C_{2-6}$alkenyl" as a group or part of a group defines straight and branched chained saturated hydrocarbon radicals having from 2 to 6 carbon atoms containing at least one double bond such as, for example, ethenyl, propenyl, butenyl, pentenyl, hexenyl and the like.

The term "$C_{2-6}$alkynyl" as a group or part of a group defines straight and branched chained saturated hydrocarbon radicals having from 2 to 6 carbon atoms containing at least one triple bond such as, for example, ethynyl, propynyl, butynyl, pentynyl, hexynyl and the like.

The term "$C_{3-7}$cycloalkyl" as a group or part of a group is generic to cyclopropyl, cyclobutyl, cyclopentyl, cyclohexyl or cycloheptyl.

The term "aryl" as a group or part of a group is meant to include phenyl and naphtyl which both may be optionally substituted with one or more substituents independently selected from $C_{1-6}$alkyl, $C_{1-6}$alkyloxy, amino$C_{1-6}$alkyl, halogen, hydroxy, optionally mono- or disubstituted amino, nitro, cyano, halo$C_{1-6}$alkyl, carboxyl, $C_{1-6}$alkoxy-carbonyl, $C_{3-7}$cycloalkyl, Het$^1$, optionally mono- or disubstituted aminocarbonyl, methylthio, methylsulfonyl, and phenyl optionally substituted with one or more substituents selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$ alkoxycarbonyl, $C_{3-7}$cycloalkyl, Het$^1$, optionally mono- or disubstituted aminocarbonyl, methylthio and methylsulfonyl; whereby the optional substituents on any amino function are independently selected from $C_{1-6}$alkyl, $C_{1-6}$alkyloxy-A-, Het$^1$-A-, Het$^1$$C_{1-6}$alkyl, Het$^1$$C_{1-6}$alkyl-A-, Het$^1$oxy-A-, Het$^1$oxy$C_{1-4}$alkyl-A-, phenyl-A-, phenyloxy-A-, phenyloxy$C_{1-4}$alkyl-A-, phenyl$C_{1-6}$alkyl-A-, $C_{1-6}$alkyloxycarbonylamino-A-, amino-A-, amino$C_{1-6}$alkyl and amino$C_{1-6}$alkyl-A- whereby each of the amino groups may optionally be mono- or where possible di-substituted with $C_{1-4}$alkyl and whereby A is as defined above.

The term "halo$C_{1-6}$alkyl" as a group or part of a group is defined as $C_{1-6}$alkyl substituted with one or more halogen atoms, preferably, chloro or fluoro atoms, more preferably fluoro atoms. Polyhalo$C_{1-4}$alkyl as a group or as part of a group is defined as $C_{1-4}$alkyl substituted with 2 or more halogen atoms. Preferred halo$C_{1-6}$alkyl group include for instance trifluoromethyl and difluoromethyl.

The term "Het$^1$" as a group or part of a group is defined as a saturated or partially unsaturated monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more carbon atoms by $C_{1-6}$alkyl, $C_{1-6}$alkyloxy, amino$C_{1-6}$alkyl, halogen, hydroxy, oxo, optionally mono- or disubstituted amino, optionally mono- or disubstituted aminoalkyl, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 14 ring members; whereby the optional substituents on any amino function are independently selected from $C_{1-6}$alkyl, $C_{1-6}$alkyloxy-A-, Het$^2$-A-, Het$^2$$C_{1-6}$alkyl, Het$^2$$C_{1-6}$alkyl-A-, Het$^2$oxy-A-, Het$^2$oxy$C_{1-4}$alkyl-A-, aryl-A-, aryloxy-A-, aryloxy$C_{1-4}$alkyl-A-, aryl$C_{1-6}$alkyl-A-, $C_{1-6}$alkyloxycarbonylamino-A-, amino-A-, amino$C_{1-6}$alkyl and amino$C_{1-6}$alkyl-A- whereby each of the amino groups may optionally be mono- or where possible di-substituted with $C_{1-4}$alkyl and whereby A is as defined above.

The term "Het$^2$" as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more carbon atoms by $C_{1-6}$alkyl, $C_{1-16}$alkyloxy, amino$C_{1-6}$alkyl, halogen, hydroxy, optionally mono- or disubstituted amino, nitro, cyano, halo$C_{1-6}$alkyl, carboxyl, $C_{1-6}$ alkoxycarbonyl, $C_{3-7}$cycloalkyl, optionally mono- or disubstituted aminocarbonyl, methylthio, methylsulfonyl, aryl, Het$^1$ and an aromatic monocyclic, bicyclic or tricyclic heterocycle having 3 to 12 ring members; whereby the optional substituents on any amino function are independently selected from $C_{1-6}$alkyl, $C_{1-6}$alkyloxy-A-, Het$^1$-A-, Het$^1$$C_{1-6}$alkyl, Het$^1$$C_{1-6}$alkyl-A-, Het$^1$oxy-A-, Het$^1$oxy$C_{1-4}$alkyl-A-, aryl-A-, aryloxy-A-, aryloxy$C_{1-4}$alkyl-A-, aryl$C_{1-6}$alkyl-A-, $C_{1-6}$alkyloxycarbonylamino-A-, amino-A-, amino$C_{1-6}$alkyl and amino$C_{1-6}$alkyl-A- whereby each of the amino groups may optionally be mono- or where possible di-substituted with $C_{1-4}$alkyl and whereby A is as defined above.

As used herein, the term (=O) forms a carbonyl moiety with the carbon atom to which it is attached. The term (=O) forms a sulfoxide with the sulfur atom to which it is attached. The term (=O)$_2$ forms a sulfonyl with the sulfur atom to which it is attached. As used herein, the term (=S) forms a thiocarbonyl moiety with the carbon atom to which it is attached.

As used herein before, the term "one or more" covers the possibility of all the available C-atoms, where appropriate, to be substituted, preferably, one, two or three.

When any variable (e.g. halogen or $C_{1-4}$alkyl) occurs more than one time in any constituent, each definition is independent.

Lines drawn from substituents into ring systems indicate that the bond may be attached to any of the suitable ring atoms.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmaco-logical Basis of Therapeutics, 8$^{th}$ ed, McGraw-Hill, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs of the compounds of the present invention include those compounds wherein for instance a hydroxy group, such as the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793 and WO 99/33792 all incorporated herein by reference.

Prodrugs are characterized by excellent aqueous solubility, increased bioavailability and are readily metabolized into the active inhibitors in vivo.

For therapeutic use, the salts of the compounds of formula (I) are those wherein the counterion is pharmaceutically or physiologically acceptable. However, salts having a pharmaceutically unacceptable counterion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of formula (I) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms which the compounds of the present invention are able to form. Examples of such forms are e.g. hydrates, alcoholates and the like. Generically they also are called solvates.

The N-oxide forms of the present compounds are meant to comprise the compounds of formula (I) wherein one or several nitrogen atoms are oxidized to the so-called N-oxide.

The present compounds may also exist in their tautomeric forms. Such forms, although not explicitly indicated in the above formula are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods which may advantageously be employed are, for example, selective crystallization and chromatography, e.g. column chromatography.

It is clear to a person skilled in the art that the compounds of formula (I) contain at least one asymmetric center and thus may exist as different stereoisomeric forms. This asymmetric center is indicated with a asterisk (*) in the figure below.

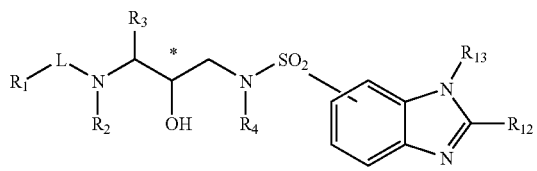

The absolute configuration of each asymmetric center that may be present in the compounds of formula (I) may be indicated by the stereochemical descriptors R and S, this R and S notation corresponding to the rules described in Pure Appl. Chem. 1976, 45, 11-30. The carbon atom marked with the asterisk (*) preferably has the R configuration.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", or "the present compounds" or similar term is meant to include the compounds of general formula (I), their N-oxides, salts, stereoisomeric forms, racemic mixtures, pro-drugs, esters and metabolites, as well as their quaternized nitrogen analogues.

An interesting group of compounds are those compounds of formula (I) wherein
L is —C(=O)—, —O—C(=O)—, —NR$_8$—C(=O)—, —O—C$_{1-6}$alkanediyl-C(=O)—, —NR$_8$—C$_{1-6}$alkanediyl-C(=O)—, —S(=O)$_2$—, —O—S(=O)$_2$—, —NR$_8$—S(=O)$_2$—, —NR$_8$—C$_{1-6}$alkanediyl-S(=O)$_2$—, whereby either the C(=O) group or the S(=O)$_2$ group is attached to the NR$_2$ moiety.

A particular group of compounds are those compounds of formula (I) wherein one or more of the following restrictions apply:
R$_1$ is hydrogen, Het$^1$, Het$^2$, aryl, Het$^1$C$_{1-6}$alkyl, Het$^2$C$_{1-6}$alkyl, arylC$_{1-6}$alkyl, more in particular, R$_1$ is hydrogen, a saturated or partially unsaturated monocyclic or bicyclic heterocycle having 5 to 8 ring members, which contains one or more heteroatom ring members selected from nitrogen, oxygen or sulfur and which is optionally substituted; phenyl optionally substituted with one or more substituents; an aromatic monocyclic heterocycle having 5 to 6 ring members, which contains one or more heteroatom ring members selected from nitrogen, oxygen or sulfur and which is optionally substituted on one or more carbon atoms; or C$_{1-6}$alkyl substituted with an aromatic monocyclic heterocycle having 5 to 6 ring members, which contains one or more heteroatom ring members selected from nitrogen, oxygen or sulfur and which is optionally substituted on one or more carbon atoms;
R$_2$ is hydrogen;
L is —C(=O)—, —O—C(=O)—, —O—C$_{1-6}$alkanediyl-C(=O)—, more in particular, L is —C(=O)—, —O—C(=O)—, —O—CH$_2$—C(=O)—, whereby in each case the C(=O) group is attached to the NR$_2$ moiety;
R$_3$ is arylC$_{1-4}$alkyl, in particular, arylmethyl, more in particular phenylmethyl;
R$_4$ is optionally substituted C$_{1-6}$alkyl, in particular C$_{1-6}$alkyl optionally substituted with aryl, Het$^1$, Het$^2$, C$_{3-7}$cycloalkyl or amino optionally mono- or disubstituted where the substituents are selected from C$_{1-4}$alkyl, aryl, Het$^1$ and Het$^2$;
R$_5$ is hydrogen, hydroxy, C$_{1-6}$alkyl, Het$^1$C$_{1-6}$alkyl, Het$^2$C$_{1-6}$alkyl, aminoC$_{1-6}$alkyl whereby the amino group may optionally be mono- or di-substituted with C$_{1-4}$alkyl;
R$_6$ is C$_{1-6}$alkyloxy, Het$^1$, Het$^1$oxy, Het$^2$, Het$^2$oxy, aryl, aryloxy, aryloxyC$_{1-4}$alkyl, C$_{1-4}$alkyloxyaryl, C$_{1-4}$alkyloxy-Het$^1$, C$_{1-4}$alkyloxyHet$^2$, C$_{1-4}$alkyloxycarbonyl-amino, aminoC$_{1-4}$alkylamino, amino or aminoC$_{1-4}$alkyloxy and in case A is other than C$_{1-6}$alkanediyl, then R$_6$ may also be C$_{1-6}$alkyl, Het$^1$C$_{1-4}$alkyl, Het$^1$oxyC$_{1-4}$alkyl, Het$^2$C$_{1-4}$alkyl, Het$^2$oxyC$_{1-4}$alkyl, arylC$_{1-4}$alkyl, aryloxyC$_{1-4}$alkyl or aminoC$_{1-4}$alkyl; whereby each amino group may optionally be mono- or where possible disubstituted with C$_{1-4}$alkyl;
R$_5$ and -A-R$_6$ taken together with the nitrogen atom to which they are attached may also form Het$^1$ or Het$^2$;
R$_{12}$ is H, —NH$_2$, —N(R$_5$)(AR$_6$), —C$_{1-6}$alkyl or C$_{1-6}$alkyl —W—R$_{14}$, wherein said C$_{1-6}$alkyl is optionally substituted with halogen, hydroxy, aryl, heteroaryl, Het$^1$, Het$^2$, or amino wherein said amino is optionally mono- or di-substituted with C$_{1-4}$alkyl;
A is C$_{1-6}$ alkanediyl, —C(=O)—, C$_{1-6}$alkanediyl-C(=O)—;
W is oxy, carbonyl, oxycarbonyl, carbonyloxy, oxycarbonyloxy, amino, aminocarbonyl, carbonylamino or sulphur;
R$_{13}$ is H, C$_{1-6}$-alkyl, optionally substituted by aryl, Het$^1$, Het$^2$, hydroxy, halogen, amino whereby the amino group may be optionally be mono- or di-substituted with C$_{1-4}$alkyl;
R$_{14}$ is C$_{1-6}$alkyl, aryl Het$^1$ or Het$^2$.

An interesting group of compounds are those compounds of formula (I) wherein one or more of the following restrictions apply
R$_1$ is thiazolyl, hexahydrofuro[2,3-b]furan-3-yl, pyrrolidinyl or phenyl which is mono- di- or trisubstituted, wherein the substituents are selected from the group consisting of methyl, nitro, amino, mono or dimethylamino, hydroxy, aminomethyl, wherein at least one of said substituents is in ortho vis-à-vis the R$_1$-L bond.
L is —O—C(=O)—, —O—CH$_2$—C(=O)—, —CH$_2$—O—C(=O)—.

A special group of compounds are those compounds of formula (I) wherein R$_1$ is Het$^1$, aryl, Het$^2$C$_{1-6}$alkyl; R$_2$ is hydrogen; L is —C(=O)—, —O—C(=O)—, —O—CH$_2$—C(=O)—, whereby in each case the C(=O) group is attached to the NR$_2$ moiety; R$_3$ is phenylmethyl; and R$_4$ is C$_{1-6}$alkyl.

Another interesting group of compounds are those compounds of formula (I) wherein L is —O—C$_{1-6}$alkanediyl-C(=O)—.

Another interesting group of compounds are those compounds of formula (I) wherein R$_{12}$ is H, —NH$_2$, —N(R$_5$) (AR$_6$), —C$_{1-6}$alkyl or C$_{1-6}$alkyl —W—R$_{14}$, wherein said C$_{1-6}$alkyl is optionally substituted with halogen, hydroxy, aryl, heteroaryl, Het$^1$, Het$^2$, or amino optionally mono- or di-substituted with C$_{1-4}$alkyl;
A is C$_{1-6}$ alkanediyl or —C(=O)—; R$_5$ is hydrogen, methyl, Het$^1$C$_{1-6}$alkyl, aminoC$_{1-6}$alkyl whereby the amino group may optionally be mono- or di-substituted with C$_{1-4}$alkyl;
R$_6$ is C$_{1-6}$alkyloxy, Het$^1$, amino; and in case -A- is other than $C_{1-6}$alkanediyl then $R_6$ may also be $C_{1-6}$alkyl, $Het^1$ $C_{1-4}$alkyl or amino$C_{1-4}$alkyl; whereby each of the amino groups may optionally be substituted;

W is oxycarbonyloxy;

$R_{14}$ is $Het^1$.

Another interesting group of compounds are those compounds of formula (I) wherein $R_{12}$ is —N($R_5$)(A$R_6$);

A is $C_{1-6}$alkanediyl or —C(=O)—; $R_5$ is hydrogen; $R_6$ is $C_{1-6}$alkyloxy, $Het^1$, $C_{1-4}$alkyloxy-aryl, amino, amino$C_{1-4}$ alkylamino, amino$C_{1-4}$alkyloxy; and in case -A- is —C(=O)— then $R_6$ may also be $C_{1-6}$alkyl, $Het^1C_{1-4}$alkyl, or amino$C_{1-4}$alkyl; whereby each of the amino groups may optionally be substituted with $C_{1-4}$alkyl.

Another interesting group of compounds are those compounds of formula (I) wherein A is $C_{1-6}$alkanediyl or —C(=O)—;

$R_5$ is hydrogen, $C_{1-6}$alkyl, $Het^1C_{1-6}$-alkyl, $Het^2C_{1-6}$alkyl, amino$C_{1-6}$alkyl whereby the amino group may optionally be mono- or di-substituted with $C_{1-4}$alkyl; and in case -A- is —C(=O)— then $R^6$ is $C_{1-6}$alkyloxy, $Het^1$, $Het^1$oxy or $Het^2$oxy, aryl, $Het^1C_{1-4}$alkyl, $Het^1$oxy$C_{1-4}$ alkyl, $Het^2C_{1-4}$alkyl, $Het^2$oxy$C_{1-4}$alkyl, aryl$C_{1-4}$alkyl, aryloxy$C_{1-4}$alkyl or amino$C_{1-4}$alkyl; and in case -A- is $C_{1-16}$ alkanediyl then $R^6$ is amino, $C_{1-6}$alkyloxy, $Het^1$, $Het^1$oxy or $Het^2$oxy; and in case -A- is $C_{1-6}$alkanediyl-C(=O)— then $R_6$ is $C_{1-6}$alkyloxy, $Het^1$, $Het^1$oxy or $Het^2$oxy, aryl, $C_{1-6}$alkyl, $Het^1C_{1-4}$ alkyl, $Het^1$oxy$C_{1-4}$alkyl, $Het^2C_{1-4}$alkyl, $Het^2$oxy$C_{1-4}$alkyl, aryl$C_{1-4}$alkyl, aryloxy$C_{1-4}$alkyl or amino$C_{1-4}$alkyl;

whereby each of the amino groups in the definition of $R_6$ may optionally be substituted with one or more substituents selected from $C_{1-4}$alkyl, $C_{1-4}$alkylcarbonyl, $C_{1-4}$alkyloxycarbonyl, aryl, arylcarbonyl, aryloxycarbonyl, $Het^1$, $Het^2$, aryl$C_{1-4}$alkyl, $Het^1C_{1-4}$alkyl or $Het^2C_{1-4}$alkyl; and $R_5$ and -A-$R_6$ taken together with the nitrogen atom to which they are attached may also form $Het^1$ whereby $Het^1$ is substituted by at least an oxo group.

Another interesting group of compounds are those compounds of formula (I) wherein $R_{13}$ is $C_{1-4}$alkyl preferably methyl, ethyl or isobutyl; optionally substituted with aryl preferably phenyl, $Het^1$ preferably pyrrolidinyl, $Het^2$ preferably imidazolyl or pyridinyl, or amino; wherein the amino group is optionally substituted with $C_{1-4}$alkyl.

Also a special group of compounds are those compounds of formula (I) wherein $R_{12}$ is H, —NH$_2$, —N($R_5$)(A$R_6$), —C$_{1-6}$alkyl or $C_{1-6}$alkyl-W—$R_{14}$, wherein said $C_{1-6}$alkyl is optionally substituted with hydroxy or amino wherein said amino is optionally mono- or di-substituted with $C_{1-4}$alkyl;
A is $C_{1-6}$ alkanediyl or —C(=O)—; $R_5$ is hydrogen, methyl, $Het^1C_{1-6}$alkyl, amino$C_{1-6}$alkyl whereby the amino group may optionally be mono- or di-substituted with $C_{1-4}$alkyl; $R_6$ is $C_{1-6}$alkyloxy, $Het^1$, amino; and in case -A- is other than $C_{1-6}$alkanediyl then $R_6$ may also be $C_{1-6}$alkyl, $Het^1C_{1-4}$alkyl or amino$C_{1-4}$alkyl; whereby each of the amino groups may optionally be substituted;

$R_{13}$ is H, $C_{1-6}$-alkyl, optionally substituted by aryl, $Het^1$, $Het^2$, hydroxy, halogen, amino whereby the amino group may be optionally be mono- or di-substituted with $C_{1-4}$alkyl.

$R_{14}$ is alkyl, aryl $Het^1$, $Het^2$.

Another interesting group of compounds are those compounds of formula (I) wherein $R_1$ hydrogen, $C_{1-6}$alkyl, $C_{2-6}$alkenyl, aryl$C_{1-6}$alkyl, $C_{3-7}$cycloalkyl, $C_{3-7}$cycloalkyl-$C_{1-6}$alkyl, aryl, $Het^1$, $Het^1C_{1-6}$alkyl, $Het^2$, $Het^2C_{1-6}$alkyl; wherein $Het^1$ is a saturated or partially unsaturated monocyclic heterocycle having 5 or 6 ring members, which contains one or more heteroatom ring members selected from nitrogen, oxygen or sulfur and which is optionally substituted on one or more carbon atoms.

Another interesting group of compounds are those compounds of formula (I) wherein:

$R_{13}$ is H, $C_{1-6}$-alkyl, optionally substituted by aryl, $Het^1$, $Het^2$, amino whereby the amino group may be optionally be mono- or di-substituted with $C_{1-4}$alkyl;

$R_{12}$ is H, —NH$_2$, —N($R_5$)(A$R_6$), —C$_{1-6}$alkyl or $C_{1-6}$alkyl-W—$R_{14}$, wherein said $C_{1-6}$alkyl is optionally substituted with hydroxy or amino wherein said amino is optionally mono- or di-substituted with $C_{1-4}$alkyl;

A is $C_{1-6}$alkanediyl, —C(=O)—, $C_{1-6}$alkanediyl-C(=O)—, $R_5$ is hydrogen, hydroxy, $C_{1-6}$alkyl, $Het^1C_{1-6}$alkyl, $Het^2C_{1-6}$ alkyl, amino$C_{1-6}$alkyl whereby the amino group may optionally be mono- or di-substituted with $C_{1-4}$alkyl;

$R_6$ is $C_{1-6}$alkyloxy, $Het^1$, $Het^1C_{1-4}$alkyl, $Het^1$oxy, $Het^1$oxy $C_{1-4}$alkyl, $Het^2$, $Het^2C_{1-4}$alkyl, $Het^2$oxy, $Het^2$oxy$C_{1-4}$ alkyl, aryl, aryloxy, aryloxy$C_{1-4}$alkyl, aryl$C_{1-4}$alkyl, $C_{1-6}$alkyloxycarbonylamino, amino or amino$C_{1-4}$alkyl whereby each amino group may optionally be mono- or where possible di-substituted with $C_{1-4}$alkyl; and $R_6$ may also be hydrogen in case -A- is $C_{1-6}$alkanediyl;

$R_5$ and -A-$R_6$ taken together with the nitrogen atom to which they are attached may also form $Het^1$ or $Het^2$;

W is oxy, carbonyl, oxycarbonyl, carbonyloxy, oxycarbonyloxy, amino, aminocarbonyl, carbonylamino or sulphur;

$R_{14}$ is alkyl, aryl $Het^1$ or $Het^2$.

Another interesting group of compounds are those compounds of formula (I) wherein both $R_{12}$ and $R_{13}$ are present.

An interesting group of compounds are those compounds of the formula (I) wherein:

$R_1$ is a bicyclic heterocycle comprising at least 7 atoms, of which at least one is O;

L is —O—C(=O)—, —C(=O)—, —CH$_2$—O—C(=O)— or —O—CH$_2$—C(=O)—;

$R_2$ is —H;

$R_3$ is $C_{1-4}$ alkylphenyl;

$R_4$ is $C_4$ alkyl;

$R_{12}$ is —H; —NH$_2$—N($R_5$)(A$R_6$), —C$_{1-6}$alkyl or $C_{1-6}$alkyl —W—$R_{14}$, wherein said $C_{1-6}$alkyl is optionally substituted with hydroxy or amino wherein said amino is optionally mono- or di-substituted with $C_{1-4}$alkyl;

A is $C_{1-6}$alkanediyl or —C(=O)—;

$R_5$ is hydrogen;

$R_6$ is $C_{1-6}$alkyloxy, $Het^1$, amino; and in case -A- is other than $C_{1-6}$alkanediyl then $R_6$ may also be $C_{1-6}$alkyl, $Het^1C_{1-4}$alkyl or amino$C_{1-4}$alkyl; whereby each of the amino groups may optionally be substituted;

W is oxycarbonyloxy;

$R_{14}$ is $Het^1$;

$R_{13}$ is H, $C_{1-4}$alkyl, $C_{1-4}$alkylaryl, $C_{1-4}$alkyl$Het^1$, $C_{1-4}$alkyl-$Het^2$.

An interesting group of compounds are those compounds of the formula (I) wherein:

$R_1$ is a bicyclic heterocycle comprising at least 7 atoms, of which at least one is O;

L is —O—C(=O)—, —C(=O)—, —CH$_2$—O—C(=O)— or —O—CH$_2$—C(=O)—;

$R_2$ is —H;

$R_3$ is $C_{1-4}$ alkylphenyl;

$R_4$ is $C_4$ alkyl;

$R_{12}$ is H;

$R_{13}$ is $C_{1-4}$ alkylaryl, $C_{1-4}$ alkyl$Het^1$, $C_{1-4}$ alkyl$Het^2$.

An interesting group of compounds are those compounds of formula (I) wherein one or more of the following restrictions apply R₁ is thiazolyl, hexahydro furo[2,3-b]furan-3-yl, pyrrolidinyl or phenyl which is mono- di- or trisubstituted, wherein the substituents are selected from the group consisting of methyl, nitro, amino, mono or dimethylamino, hydroxy, aminomethyl, wherein at least one of said substituents is in ortho vis-à-vis the R₁-L bond.

L is —O—C(=O)—, —O—CH₂—C(=O)—, —CH₂—O—C(=O)—;

R₁₂ is hydrogen, methyl, methylcarbonylamino, methyloxycarbonylamino;

R₁₃ is hydrogen, methyl, isobutyl, phenylmethyl, phenylethyl.

Another interesting group of compounds are the compounds of formula (I) of structure 1 to 64 as shown in table 1 and 2. An interesting subgroup thereof are the compounds of formula (I) having a number 1-13, 15, 17-19, 21, 22, 24, 37 and 64.

An interesting group of compounds are the compounds of formula (I) which contain at least one group selected from thiazolyl, imidazolyl or pyridinyl.

The invention also relates to the methods of synthesis of the compounds of the present invention.

The invention further relates to the intermediates in the synthesis of the compounds of the present invention. Interesting intermediates are the intermediates of formula D-2, E-2, F-2, in particular F-2. Another group of interesting intermediates are those intermediates of formula D-4, F-4, in particular F-4. A further interesting group of intermediates are those intermediates of formula F-5, G-5, and H-5, in particular H-5. Also interesting intermediates are those of formula G-5, H-5 and J-7.

The invention also relates to a compound of formula (I) obtainable by a process as shown in schemes 1 to 7.

Preferably the compounds of formula (I) have the stereochemistry as indicated in formula (I').

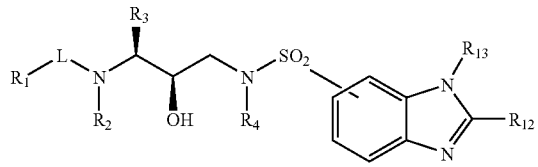

The compounds of formula (I) can generally be prepared using procedures analogous to those procedures described in WO 95/06030, WO 96/22287, WO 96/28418, WO 96/28463, WO 96/28464, WO 96/28465, WO 99/59989 and WO 97/18205.

Particular reaction procedures to make the present compounds are described below. In the preparations described below, the reaction products may be isolated from the medium and, if necessary, further purified according to methodologies generally known in the art such as, for example, extraction, crystallization, trituration and chromatography.

The following abbreviations are used throughout the synthesis procedures. Boc: t-butyloxycarbonyl, DCM: dichloromethane, DCC: dicyclohexylcarbodiimide; DMF: dimethylformamide; EDCI: 1-(3-dimethylaminopropyl)-3-ethylcarbodiimide hydrochloric acid; HOBt: 1-hydroxy-1-H-benzotriazole; THF: tetrahydrofurane; mCPBA: metachloroperbenzoic acid. In the following synthesis all substituents R$_i$, wherein i is an integer from 1 to 14, are as defined supra, except if expressly stated otherwise, PG and PG' each independently indicate protecting groups.

Scheme 1

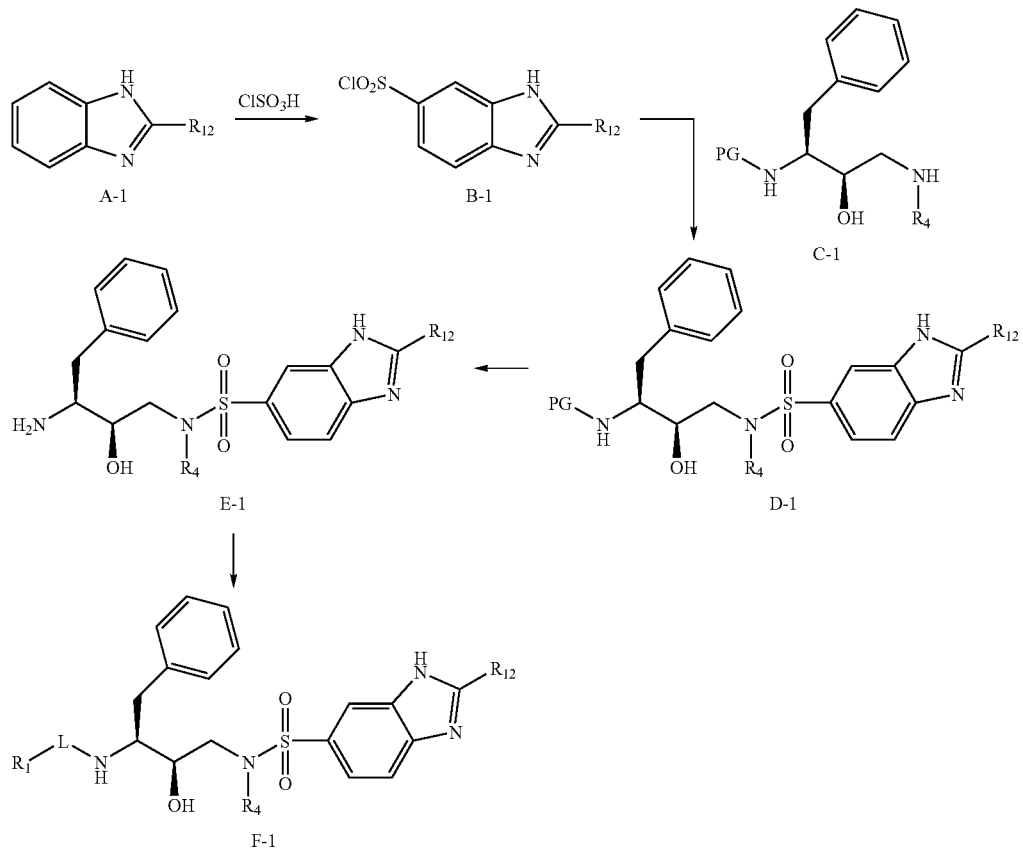

Compound A-1 was reacted with chlorosulfonic acid to yield intermediate B-1. Those skilled in the art will appreciate that this intermediate tautomerizes. The depicted B-1 intermediate is one example intermediate.

Intermediate D-1 was prepared by reacting an intermediate C-1, obtained according to the procedure described in patent WO97/18205 and also depicted in scheme 8, with an intermediate B-1, in a reaction-inert solvent such as dichloromethane, in the presence of a base such as triethylamine, at low temperature, for example 0° C.

The aminoterminal protective group in the intermediates may be a protective group known in the art such as tert-butyloxycarbonyl group. This protective group may conveniently be replaced by another suitable protective group such as phtalimido, dibenzyl or benzyloxycarbonyl.

Intermediate D-1 can be deprotected using an acid such as trifluoroacetic acid in a suitable solvent such as dichloromethane, yielding an intermediate E-1.

Alternatively, intermediates may be deprotected with a strong acid such as hydrochloric acid in isopropanol, in a suitable solvent such as a mixture of ethanol and dioxane.

The aminoterminal group may subsequently be substituted by procedures known in the art to generate F-1. As is indicated supra, the compound of formula F-1 tautomerizes, therefore, the indicated formula is one tautomer.

In a preferred embodiment the protecting group is selected from Fmoc, Acetyl, tert-Butyloxycarbonyl, Benzyloxycarbonyl-, Dibenzyl-.

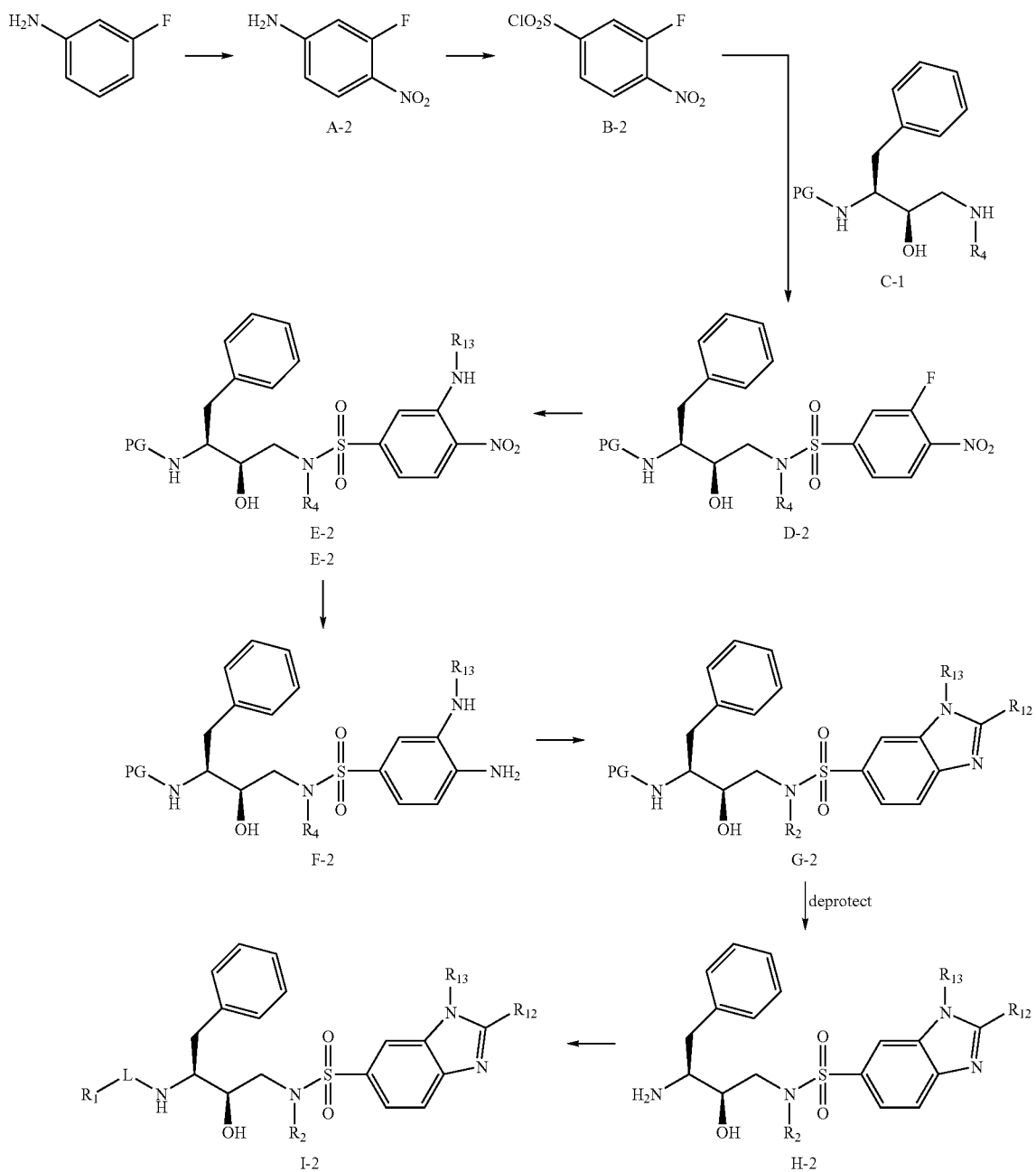

Scheme 2

3-fluoroaniline was nitrated in conditions known in the art to yield intermediate A-2, which was further reacted as described in Helvetica Chimica Acta, (1983), 66(1), p 68-75 to give intermediate B-2.

Intermediate D-2 was prepared by reacting an intermediate C-1, obtained according to the procedure described in patent WO97/18205 and also depicted in scheme 8, with an intermediate B-2, in a reaction-inert solvent such as dichloromethane, in the presence of a base such as triethylamine, at low temperature, for example 0° C.

The aminoterminal protective group in the intermediates may be a protective group known in the art such as tert-butyloxycarbonyl group. This protective group may conveniently be replaced by another suitable protective group such as phtalimido, dibenzyl or benzyloxycarbonyl.

Nucleophilic substitution of the fluorine atom by a primary amine under heating conditions led to intermediate E-2, whose nitro group was reduced to an amino group using a procedure known in the art such as catalytic hydrogenation or transfer hydrogenation, yielding intermediate F-2.

veniently be replaced by another suitable protective group such as phtalimido, dibenzyl or benzyloxycarbonyl.

Intermediate G-2 can be deprotected using an acid such as trifluoroacetic acid in a suitable solvent such as dichloromethane to yield intermediate H-2.

The aminoterminal group of H-2 may subsequently be substituted by procedures known in the art to generate the compounds of formula I-2.

Alternatively, intermediates may be deprotected with a strong acid such as hydrochloric acid in isopropanol, in a suitable solvent such as a mixture of ethanol and dioxane.

In a preferred embodiment the protecting group is selected from Fmoc, Acetyl, tert-butyloxycarbonyl, benzyloxycarbonyl-, dibenzyl-.

The procedure outlined in scheme 2 generates regioselective substitution of benzimidazol with the $R_{12}$ and $R_{13}$ substituents. If $R_{13}$ is hydrogen, the intermediates and compounds may tautomerize

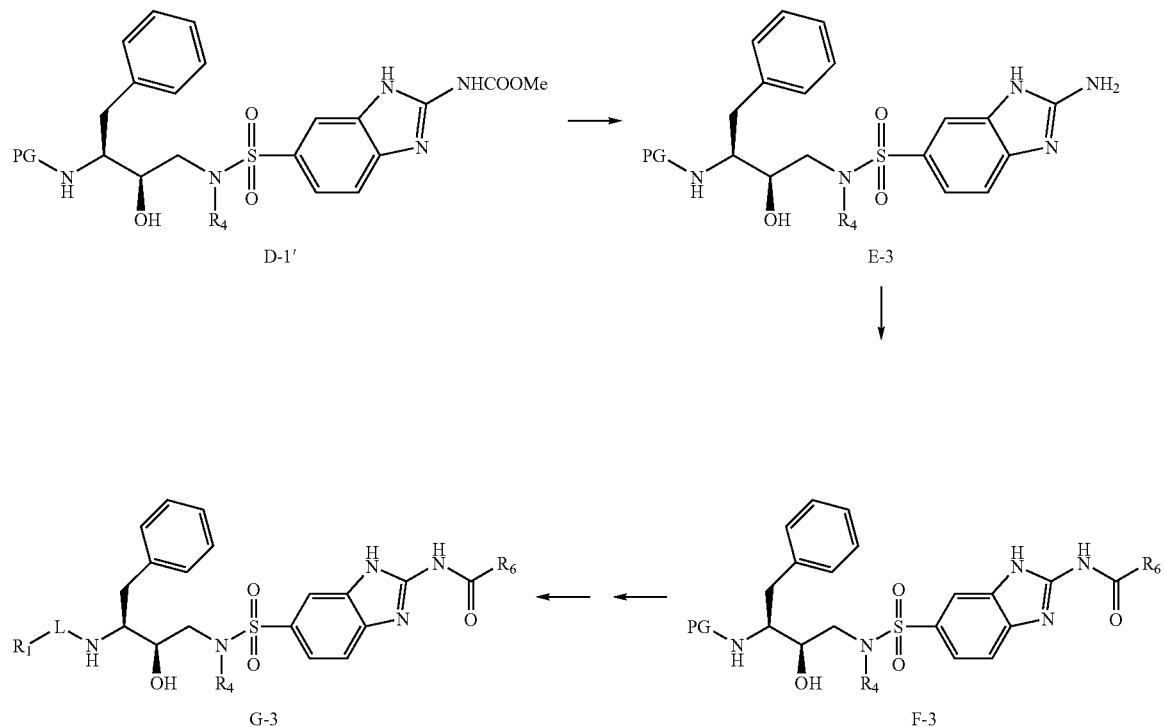

Scheme 3

Cyclisation of F-2 with methylorthoformate ($R_{12}$=H) or a carboxylic acid of formula $R_{12}$COOH($R_{12}$ differs from H) in an acidic solvent such as hydrochloric acid, or with BrCN led to compounds G-2, wherein respectively $R_{12}$=H (cyclization with methylorthoformate), $R_{12}$ differs from hydrogen (cyclization with $R_{12}$COOH, wherein $R_{12}$ differs from H) or $R_{12}$=NH$_2$ (cyclization with BrCN).

The aminoterminal protective group PG in the intermediates G-2 may be a protective group known in the art such as tert-butyloxycarbonyl group. This protective group may con- Intermediate D-1', obtained according to scheme 1, was reacted with an alkaline solution such as sodium hydroxide in methanol and water, to yield intermediate E-3, which was further acylated with acyl chlorides $R_6$COCl, in the presence of a base such as triethylamine, yielding intermediate F-3.

Intermediate F-3 was then deprotected and further substituted as described in scheme 1 to yield compounds of formula G-3.

The person skilled in the art will recognize that the intermediates in scheme 2 and compounds of formula G-3 may exist as tautomers.

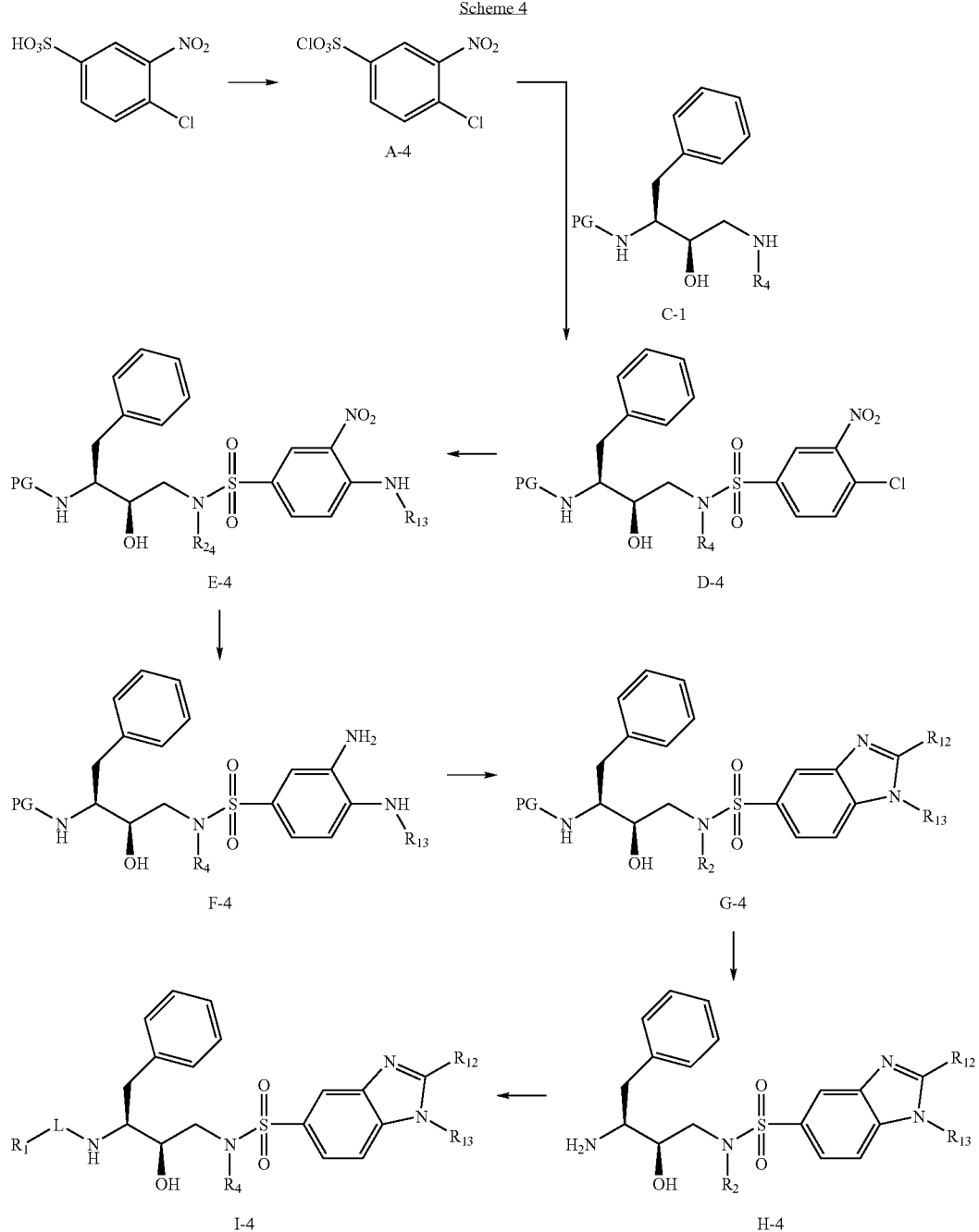

Scheme 4

Reaction of 4-chloro-3-nitrobenzene sulfonic acid with chlorosulfonic acid led to intermediate A-4.

Intermediate D-4 was prepared by reacting an intermediate C-1, obtained according to the procedure described in patent WO97/18205 and also depicted in scheme 8, with an intermediate A-4, in a reaction-inert solvent such as dichloromethane, in the presence of a base such as triethylamine, at low temperature, for example 0° C.

The aminoterminal protective group in the intermediates may be a protective group known in the art such as tert-butyloxycarbonyl group. This protective group may conveniently be replaced by another suitable protective group such as phtalimido, dibenzyl or benzyloxycarbonyl.

Nucleophilic substitution of the chlorine atom by a primary amine ($R_{13}NH_2$) under heating conditions led to intermediate E-4, whose nitro group was reduced to an amino group using a procedure known in the art such as catalytic hydrogenation or transfer hydrogenation, yielding intermediate F-4.

Cyclisation of F-4 with methylorthoformiate, a carboxylic acid of formula $R_{12}COOH$ wherein $R_{12}$ differs from hydrogen in an acidic solvent such as hydrochloric acid, or with BrCN led to final compounds G-4.

Intermediate G-4 can then be deprotected and further substituted according to the procedures as described in scheme 1 to yield final compounds I-4.

This scheme results in regioselective substitution of the benzimidazol moiety with $R_{12}$ and $R_{13}$ respectively. If $R_{13}$ is hydrogen, the intermediates and compounds of scheme 4 may exist as tautomers.

was further reduced to compound H-5. Compound H-5 can also be obtained directly from F5 by reductive amination with an aldehyde RCHO, and a reducing agent such as titanium IV isopropoxide, in an organic solvent such as DCM. R is aryl,

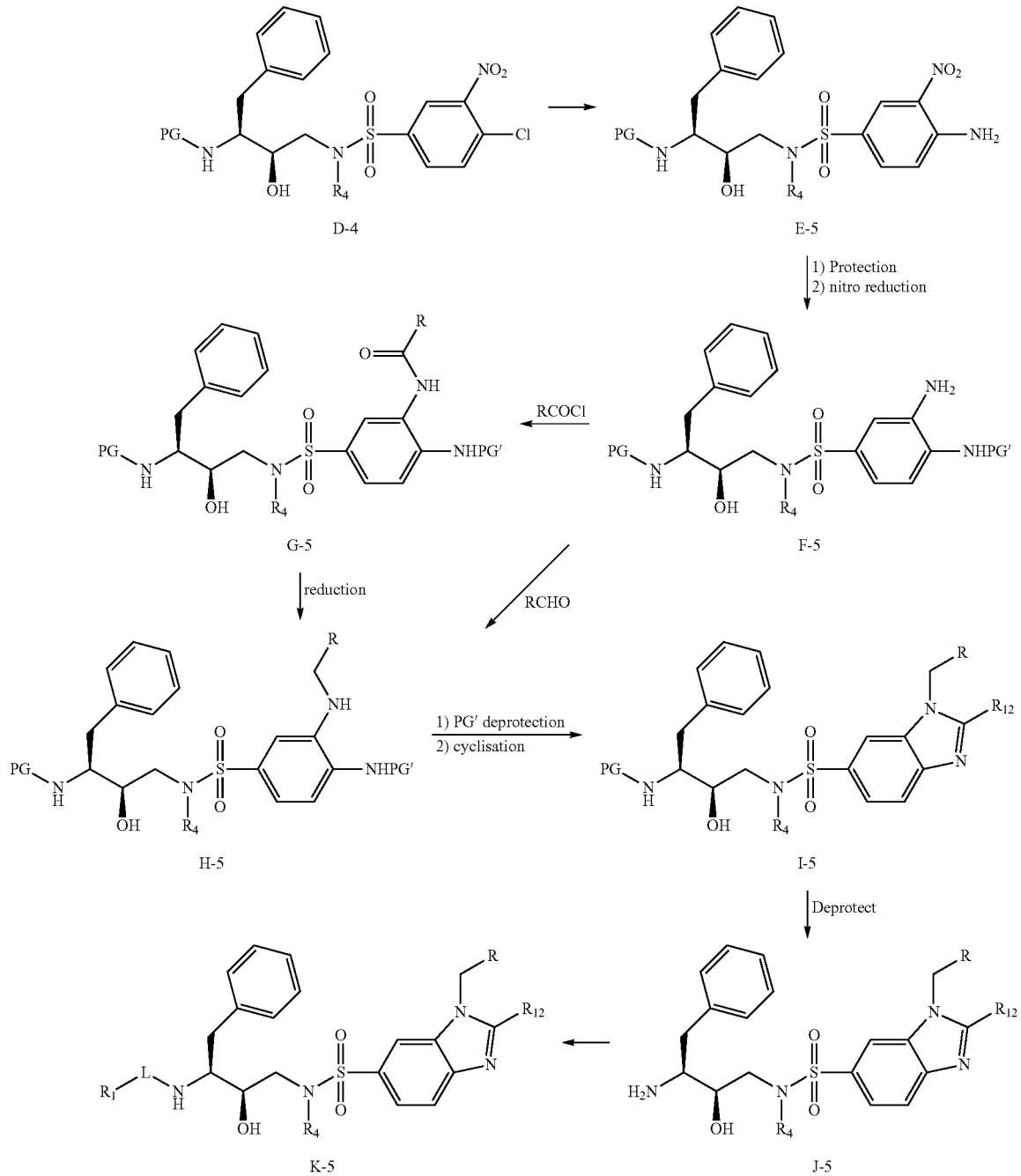

Intermediate D-4 was reacted with ammonia in a suitable solvent such as isopropanol, under heating conditions, to yield intermediate E-5. The amino group was then protected (PG') by e.g. a Boc-group, and the nitro group was reduced using conditions known in the art, for example catalytic hydrogenation, yielding compound F-5.

Reaction of compound F-5 with an acylchloride of formula RCOCl, in presence of a base such as triethylamine, in an organic solvent such as DCM, led to intermediate G-5, which $Het^1$, $Het^2$ or $C_{1-5}$alkyl optionally substituted with aryl, $Het^1$, $Het^2$, hydroxy, halogen, amino whereby the amino group may be optionally be mono- or di-substituted with $C_{1-4}$alkyl. The —$CH_2$—R moiety of intermediates H-5 to K-5 taken together is identical to the definition of $R_{13}$.

After PG' deprotection with, for example, HCl in isopropanol, compound H-5 was cyclized as previously described with methylorthoformate or a carboxylic acid $R_{12}$COOH wherein $R_{12}$ differs from hydrogen in an acidic solvent such as hydrochloric acid, or with BrCN to yield compound I-5.

Intermediate I-5 can then be deprotected and further substituted according to the methods as described in scheme 1 to yield compounds of formula K-5.

In a preferred embodiment, the amino protecting group PG is dibenzyl, removed by catalytic hydrogenation, in the presence of palladium on charcoal, in an organic solvent such as methanol.

Compound H-6 was then reduced to intermediate I-6, further deprotected using, for example, HCl in isopropanol, and cyclized as previously described in scheme 2 and 4, to yield compound J-6.

Intermediate J-6 can then be deprotected and further substituted as described in scheme 1 to yield compounds of formula L-6.

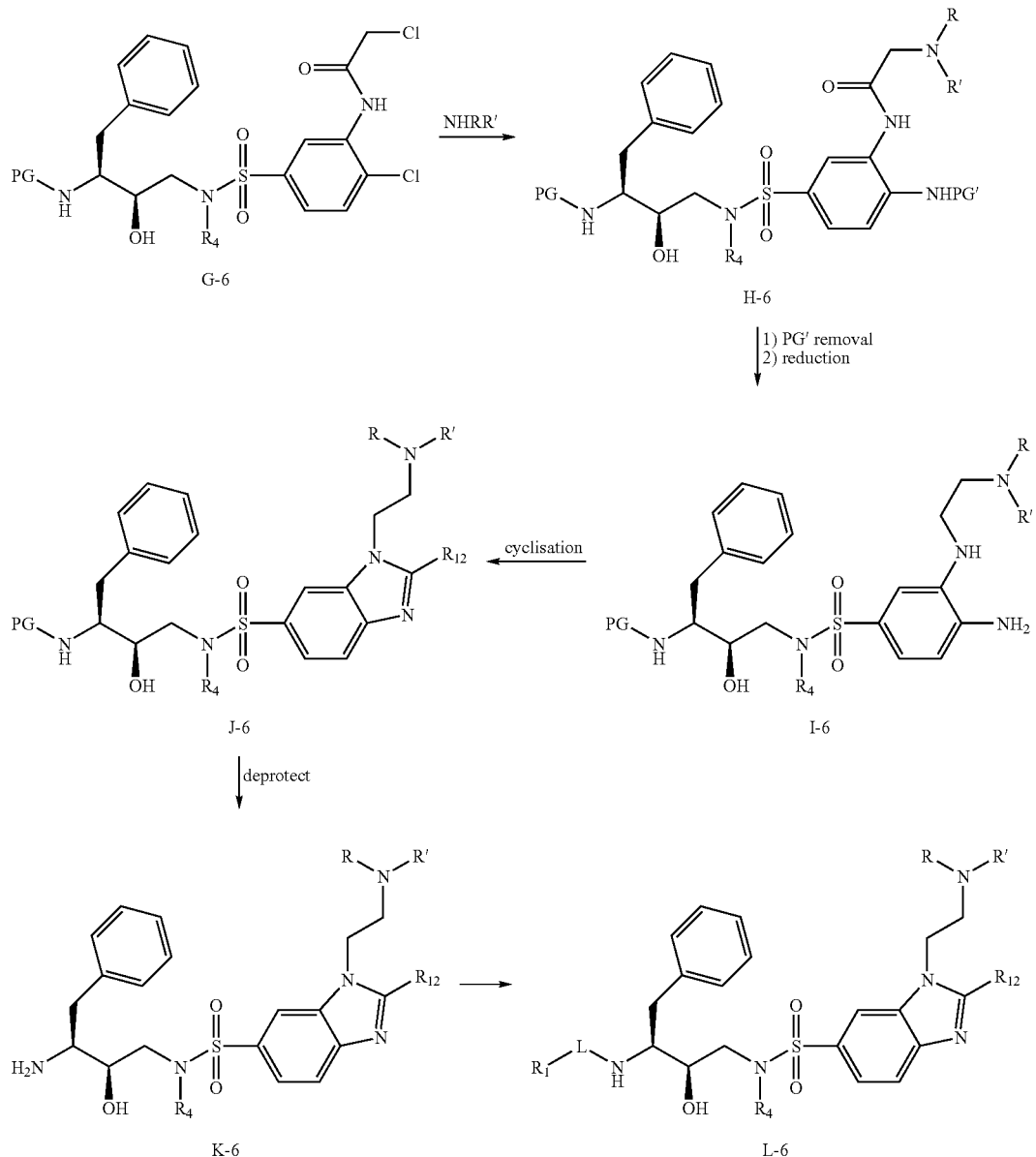

Scheme 6

Intermediate G-6, obtained as described in scheme 5 from intermediate F-5 and chloroacetic chloride in the presence of a base such as triethylamine, was substituted by an amine of formula NHRR' to yield compound H-6. R and R' are each independently H or $C_{1-4}$alkyl. PG' preferably is boc.

In an embodiment, the amino protecting group PG is dibenzyl, removed by catalytic hydrogenation, in the presence of palladium on charcoal, in an organic solvent such as methanol.

Scheme 7

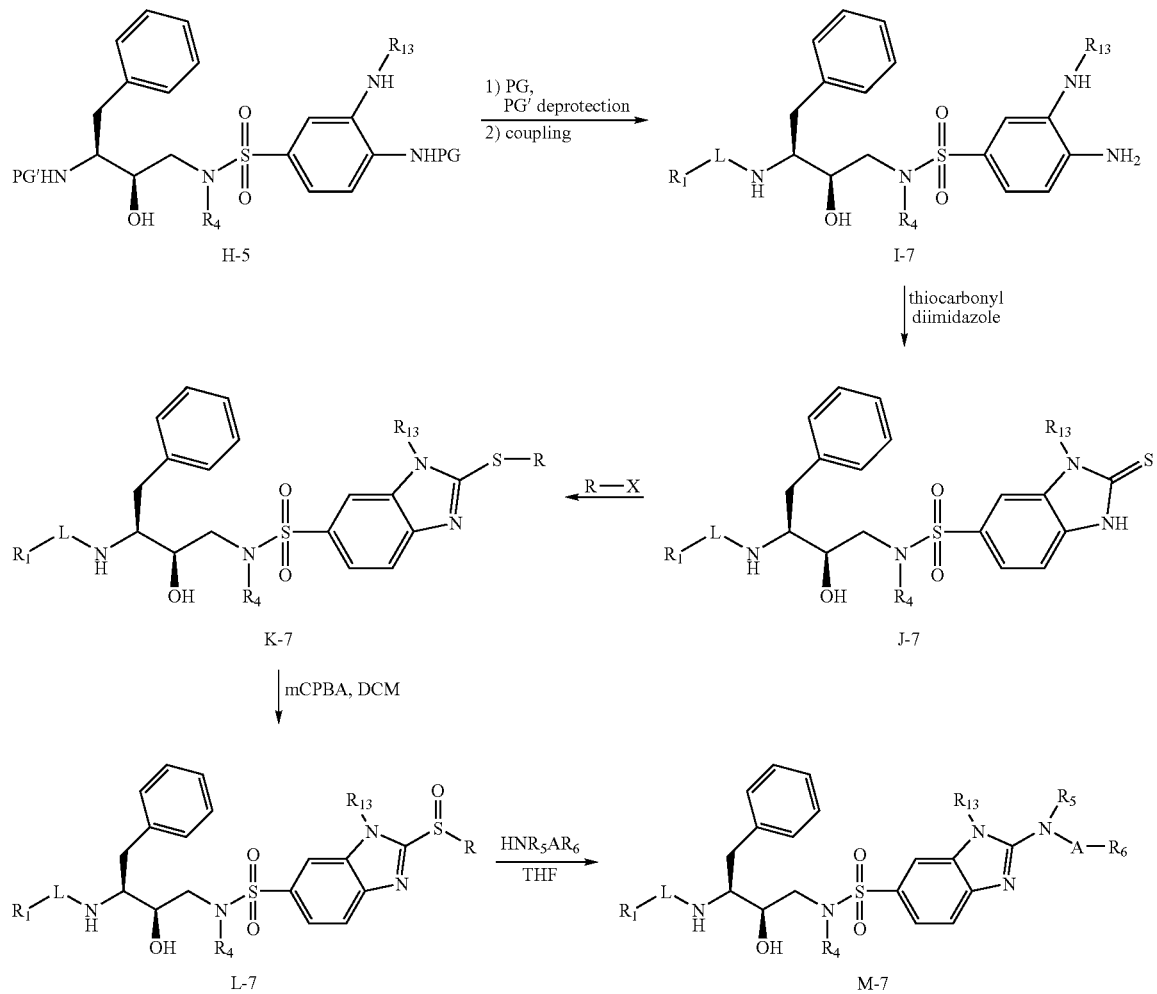

Intermediate H-5 was obtained as described in scheme 5. PG and PG' may be Boc. H-5 was deprotected using an acid for example HCl in isopropanol, and coupled with a compound of formula R$_1$-L-(leaving group), in the presence of a base such as triethylamine, in a suitable organic solvent such as DCM, leading to intermediate I-7.

Cyclisation of intermediate I-7 was achieved with thiocarbonylimidazole in a suitable organic solvent such as THF, leading to intermediate J-7, which was then reacted with an alkylhalide of formula R-X, wherein R is a C$_{1-6}$alkyl and X is an halide. An example thereof is methyliodide, in the presence of a base such as potassium carbonate in DMF.

After oxidation of intermediate K-7 with a suitable reagent such as mCPBA in DCM, the obtained methylsulfoxide group was substituted by an amine of formula HNR$_5$AR$_6$, in the presence of a base such as potassium carbonate in THF, under reflux conditions, yielding compound of formula M-7. If R$_{13}$ is hydrogen, the intermediates and compounds of scheme 7 may exist as tautomers.

Scheme 8

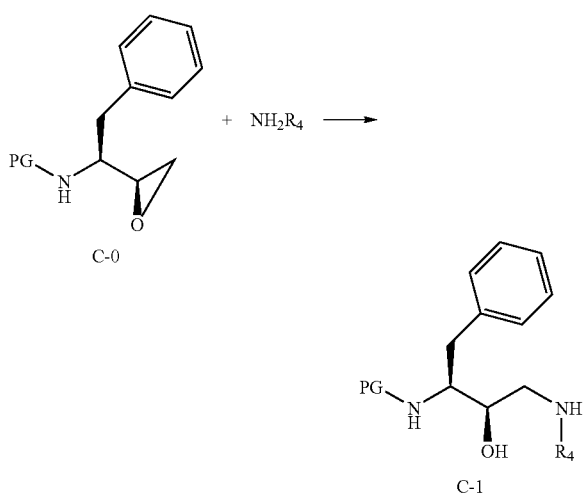

Intermediate C-1 may be prepared by reacting compound C-0 with an amine, in a suitable solvent such as isopropanol.

It will be clear for the person skilled in the art that starting from a stereospecific intermediate of formula C-0, stereoselective intermediates of formula C-1 will be obtained following reaction with a primary amine.

EXAMPLE 1

Preparation of Compound 8

Intermediate 1-e

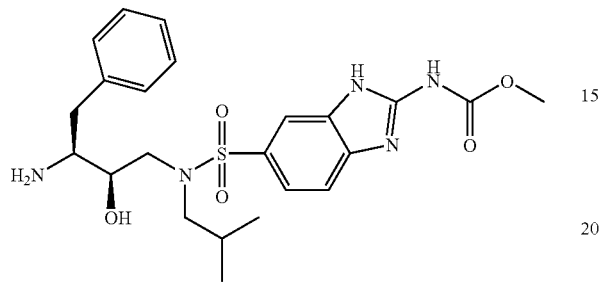

25 g of 1H-benzimidazol-2-yl-carbamic acid, methyl ester 1-a were dissolved in 45 mL of chlorosulfonic acid, at 0° C. The reaction mixture was then warmed up to 50° C. and stirred during 4 hours. The reaction mixture was poured onto a mixture of ice and water and was stirred until a white precipitate was formed. The precipitate was next filtered and washed successively with an acidic aqueous solution (pH<2), a basic aqueous solution (pH>10) and a neutral aqueous solution (pH=7 to 8), and dried in a vacuum oven, yielding 24 g (64%) of the desired intermediate 1-b, methyl[5-(chlorosulfonyl)-1H-benzimidazol-2-yl]carbamate.

2 g of intermediate 1-c [2R-hydroxy-3-[(2-methylpropyl) amino]-1S-(phenylmethyl)-propyl]carbamic acid, 1,1-dimethylethyl ester were dissolved in 50 mL of DCM. 1.8 g of triethylamine were then added to the reaction mixture, followed by portion-wise addition of 1.81 g of intermediate 1-b. After 5 hours stirring at room temperature, the reaction mixture was washed with water, dried over MgSO$_4$, filtered and evaporated to yield 3 g (85%) of the desired intermediate 1-d, [(1S,2R)-2-hydroxy-3-[[[2-[(methoxy-carbonyl)amino]-1H-benzimidazol-5-yl]sulfonyl]-(2-methylpropyl)amino]-1-(phenyl-methyl)propyl]carbamic acid, 1,1-dimethylethyl ester.

3 g of intermediate 1-d were dissolved in a mixture of 8 mL of HCl in isopropanol and mL of ethanol. The reaction mixture was stirred at room temperature overnight, then the solid was filtered off and was redissolved in a mixture DCM/saturated solution of NaHCO$_3$ in water. The organic layer was dried over MgSO$_4$ and evaporated to yield 1.4 g (60%) of the intermediate 1-e [5-[[[(2R,3S)-3-amino-2-hydroxy-4-phenylbutyl]-(2-methylpropyl)amino]sulfonyl]-1H-benzimidazol-2-yl]carbamic acid, methyl ester as a free base.

Compound 8

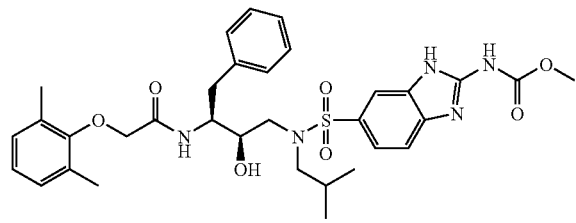

1 g of intermediate 1-e was dissolved in 20 mL of DCM. 0.37 g of 2,6-dimethyl-phenoxyacetic acid, 0.42 g of DCC and 0.27 g of HOBt were then added to the reaction mixture, which was stirred at room temperature during 4 hours. The reaction mixture was evaporated and the residue dissolved in 20 mL of ethylacetate. The reaction mixture was cooled down to 0° C. and the precipitate of dicyclohexylurea was filtered off. The organic layer was then washed with a solution of Na$_2$CO$_3$ in water, brine, dried over MgSO$_4$ and evaporated. The crude compound was purified on silica gel eluting with 5% methanol in DCM, yielding 1.29 g (97%) of the desired final compound [(1S,2R)-2-hydroxy-3-[[[2-[(methoxycarbonyl) amino]-1H-benzimidazol-5-yl]sulfonyl](2-methylpropyl) amino]-1-(phenylmethyl)propyl]-(2,6-dimethylphenoxy)acetamide (compound 8).

EXAMPLE 2

Preparation of Compound 7

Compound 7

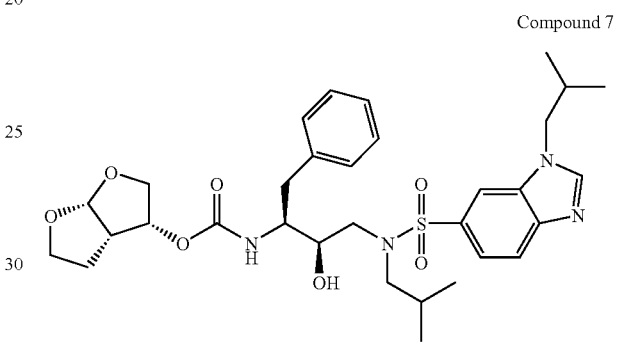

58 g of 3-fluoroaniline and 58 mL of benzaldehyde were heated at 80° C. during one hour. 200 mL of sulfuric acid were then added to the reaction mixture, cooled with an ice bath. After removing of the ice bath, the reaction mixture was further stirred at room temperature until complete dissolution of the solid. The reaction mixture was next cooled to 0° C. with an ice bath and 36 mL of nitric acid in 120 mL of sulfuric acid were added dropwise, maintaining the temperature at 0° C. After one hour of stirring at 0° C., the solid was filtered off and poured into a saturated solution of potassium carbonate in water. Ethyl acetate was then added and the two layers were separated. The aqueous phase was extracted two more times with ethyl acetate. The organic phases were collected, dried over MgSO$_4$ and evaporated. The crude compound was purified on silica gel eluting with 40% ethyl acetate in hexane, yielding 28.65 g (35%) of the desired intermediate A-2 3-fluoro-4-nitroaniline.

28.65 g of intermediate A-2 was dissolved in 230 mL of chlorhydric acid 36%. The reaction mixture was cooled to 0° C. with an ice bath and 13.7 g of sodium nitrite was added portion-wise. The reaction was maintained at 0° C. during 1.5 hours, then mixed with 145 mL of a SO$_2$ saturated acetic acid solution, containing 10.5 mL of water and 9.3 g of CuCl$_2$.2H$_2$O. After complete addition, the cooling bath was removed and the reaction mixture was stirred at room temperature during one hour, then poured onto ice. The solid was filtered off yielding 37.7 g of the intermediate B-2 3-fluoro-4-nitro-benzene sulfonyl chloride.

To a solution of 53 g of intermediate C-1 (PG=Boc, R$_4$=isobutyl) in 500 mL of THF containing 42 mL of triethylamine was added portion-wise 37.7 g of intermediate B-2. The reaction mixture was stirred at room temperature overnight then evaporated. The residue was dissolved in ethylacetate and extracted with water, then with a solution of HCl 5% in water and with a K₂CO₃ solution in water. The organic layer was then dried over MgSO₄ and evaporated. The crude compound was purified on silica gel yielding 53 g (65%) of the desired intermediate 2-a [(1S,2R)-3-[[(3-fluoro-4-nitrophenyl)-sulfonyl](2-methylpropyl)amino]-2-hydroxy-1-(phenylmethyl)propyl]carbamic acid, 1,1-dimethylethyl ester.

2 g of intermediate 2-a were dissolved in 50 mL of DMF and 1.85 mL of isopropyl-amine were added. The reaction mixture was stirred at 60° C. overnight, then concentrated and the residue treated with a mixture of EtOAc and brine. The organic layer was then dried over MgSO₄ and evaporated to yield 2 g (91%) of the desired intermediate 2-b [(1S,2R)-2-hydroxy-3-[(2-methylpropyl)[[3-(2-methylpropyl)amino-4-nitrophenyl]sulfonyl]amino]-1-(phenylmethyl)propyl]carbamic acid, 1,1-dimethylethyl ester, used without other purification in the next step.

2 g of intermediate 2-b were dissolved in 40 mL of methanol, then 1.5 g of ammonium formate and 0.2 g of palladium on charcoal (10%) were added. The reaction mixture was stirred overnight at 60° C., then 0.5 g of ammonium formate and 0.2 g of palladium on charcoal were added. After three hours, the mixture was filtered on celite and evaporated. The residue was dissolved in 50 mL of DCM, washed with a solution of Na₂CO₃ in water, then brine, dried over MgSO₄ and evaporated to yield 1.3 g (68%) of intermediate 2-[(1S, 2R)-3-[[4-amino-3-[(2-methylpropyl)amino]phenyl]sulfonyl]-(2-methylpropyl)amino]-2-hydroxy-1-(phenylmethyl)propyl]carbamic acid, 1,1-dimethylethyl ester, used without other purification in the next step.

1.3 g of intermediate 2-c was dissolved in 20 mL of ethyl orthoformate. The reaction mixture was stirred at 80° C. during 5 hours then concentrated. The residue was dissolved in ethyl acetate and washed with a solution of Na₂CO₃ in water. The organic layer was dried over MgSO₄ and evaporated. The crude compound was purified on silica gel eluting with 0 to 2% methanol in DCM, yielding 0.8 g (70%) of the desired intermediate 2-d [(1S,2R)-2-hydroxy-3-[(2-methylpropyl)[[1-(2-methylpropyl)-benzimidazol-6-yl]sulfonyl]amino]-1-(phenylmethyl)propyl]carbamic acid, 1,1-dimethylethyl ester.

2.6 g of intermediate 2-d was dissolved in 100 mL of HCl 5N in isopropanol. The reaction mixture was stirred at room temperature during 2 hours, then concentrated to yield 2.5 g (94%) of the deprotected amine as an HCl salt, N-[(2R,3S)-3-amino-2-hydroxy-4-phenylbutyl]-N-(2-methylpropyl)[1-(2-methylpropyl)benzimidazol-6-yl]-sulfonamide, hydrochloride (2-e).

2.5 g of 2-e and 1.5 mL of triethylamine were dissolved in 60 mL of DCM. 3.05 g of 1-[[(3R,3aS,6aR)-hexahydrofuro[2,3-b]furan-3-yl]oxycarbonyloxy]-2,5-pyrrolidinedione were then added and the reaction mixture was stirred at room temperature during 4 hours. The reaction mixture was then washed with a solution of Na₂CO₃ in water, then brine, dried over MgSO₄ and evaporated. The crude compound was purified on silica gel eluting with 5% methanol in DCM, yielding 1.8 g (60%) of the desired final compound [(1S,2R)-2-hydroxy-3-[(2-methylpropyl)[[1-(2-methyl-propyl)benzimidazol-6-yl]sulfonyl]amino]-1-(phenylmethyl)propyl]carbamic acid, [(3R,3aS,6aR)-hexahydrofuro[2,3-b]furan-3-yl]ester (compound 7).

EXAMPLE 3

Preparation of Compound 1

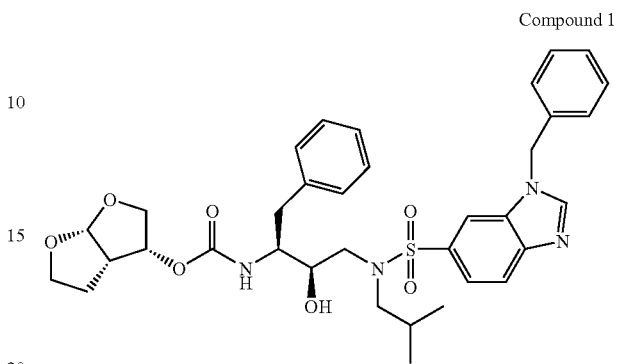

Compound 1

54 mg of intermediate D-2 (PG=Boc) were dissolved in 20 mL of THF and 11 mg of benzylamine were added. The reaction mixture was stirred at reflux during 4 hours, then concentrated. The crude compound was purified on silica gel eluting with 10% ethylacetate in hexane, yielding 60 mg of intermediate 3-a [(1S,2R)-2-hydroxy-3-[(2-methylpropyl)[[4-nitro-3-[(phenylmethyl)amino]phenyl]sulfonyl]amino]-1-(phenyl-methyl)propyl]carbamic acid, 1,1-dimethylethyl ester.

60 mg of intermediate 3-a was dissolved in 20 mL of methanol. The reaction mixture was then hydrogenated in the presence of 25 mg of palladium on charcoal (10%), at room temperature, overnight. After filtration of the catalyst, the reaction mixture was concentrated to give the intermediate 3-[(1S,2R)-3-[[[4-amino-3-[(phenylmethyl)-amino]phenyl]sulfonyl](2-methylpropyl)amino]-2-hydroxy-1-(phenylmethyl)propyl]-carbamic acid, 1,1-dimethylethyl ester which was used in the next step without further purification.

59 mg of intermediate 3-b was dissolved in 20 mL of methylorthoformate. The reaction mixture was stirred at 80° C. during 5 hours then concentrated. The residue was dissolved in ethyl acetate and washed with a solution of Na₂CO₃ in water. The organic layer was dried over MgSO₄ and evaporated to give the intermediate 3-c [(1S,2R)-2-hydroxy-3-[(2-methylpropyl)[[1-(phenylmethyl)benzimidazol-6-yl]sulfonyl]amino]-1-(phenylmethyl)propyl]carbamic acid, 1,1-dimethylethyl ester which was used in the next step without further purification.

500 mg of intermediate 3-c was reacted with 15 mL of HCl 5N in isopropanol at room temperature during 2 hours. The reaction mixture was then concentrated to give the intermediate 3-d as an HCl salt N-[(2R,3S)-3-amino-2-hydroxy-4-phenylbutyl]-N-(2-methylpropyl)[1-(phenylmethyl)benzimidazol-6-yl]sulfonamide, hydrochloride which was used in the next step without further purification.

500 mg of the previous intermediate 3-d and 85 mg of triethylamine were dissolved in 10 mL of DCM. 271 mg of 1-[[(3R,3aS,6aR)-hexahydrofuro[2,3-b]furan-3-yl]oxy-carbonyloxy]-2,5-pyrrolidinedione were then added and the reaction mixture was stirred at room temperature during 4 hours. The reaction mixture was evaporated and the crude compound was purified on silica gel eluting with 5% methanol in DCM, yielding 236 mg (35%) of the desired final compound [(1S,2R)-2-hydroxy-3-[(2-methylpropyl)[[1-(phenylmethyl)benzimidazol-6-yl]sulfonyl]amino]-1-(phenylmethyl)-propyl]carbamic acid, [(3R,3aS,6aR)-hexahydrofuro[2,3-b]furan-3-yl]ester (compound 1).

EXAMPLE 4

Preparation of Compound 2

Compound 2

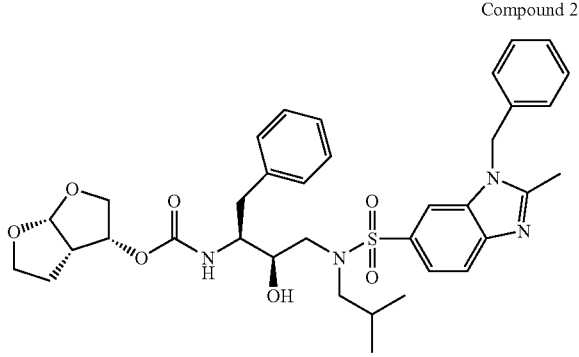

59 mg of intermediate F-2 (PG=Boc, $R_{13}$=benzyl) and 10 mg of acetic acid were stirred in 5 ml of dioxane/5 ml of 5N HCl for the weekend at 110° C. After cooling, EtOAc was added and the reaction was poured onto a mixture of ice, saturated NaHCO$_3$ solution and EtOAc. After extraction with EtOAc, the organic layer was dried and evaporated under reduced pressure to give the intermediate 4-a [(1S,2R)-2-hydroxy-3-[[[[2-methyl-1-(phenylmethyl)]benzimidazol-6-yl]sulfonyl](2-methyl propyl)amino]-1-(phenylmethyl)propyl]carbamic acid, 1,1-dimethylethyl ester which was used in the next step without further purification.

500 mg of intermediate 4-a was reacted with 15 mL of HCl 5N in isopropanol at room temperature during 2 hours. The reaction mixture was then concentrated to give intermediate 4-b as an HCl salt N-[(2R,3S)-3-amino-2-hydroxy-4-phenyl-butyl]-N-(2-methylpropyl) [[2-methyl-1-(phenylmethyl)] benzimidazol-6-yl]sulfonamide, hydrochloride which was used in the next step without further purification.

510 mg of intermediate 4-b, 271 mg of 1-[[(3R,3aS,6aR)-hexahydrofuro[2,3-b]furan-3-yl]oxycarbonyloxy]-2,5-pyrrolidinedione and 85 mg of triethylamine, were mixed in mL of DCM. The reaction mixture was stirred during 2 hours at room temperature, washed with water then evaporated. The crude compound was purified on silica gel eluting with 5% methanol in DCM, yielding 165 mg (25%) of the final compound [(1S,2R)-2-hydroxy-3-[[[[2-methyl-1-(phenylmethyl)]benzimidazol-6-yl]sulfonyl]-(2-methylpropyl)amino]-1-(phenylmethyl)propyl]carbamic acid, [(3R,3aS,6aR)-hexahydrofuro[2,3-b]furan-3-yl]ester (Compound 2).

EXAMPLE 5

Preparation of Compound 9

Compound 9

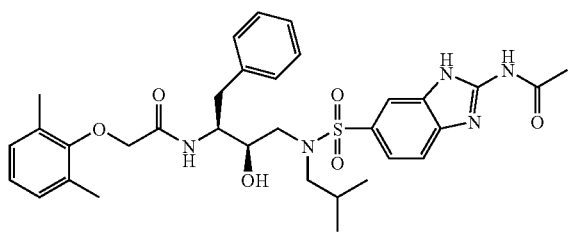

20 g of intermediate C-1. (PG=dibenzyl, $R_4$=isobutyl) were dissolved in 250 mL of DCM. 23 mL of triethylamine were then added to the reaction mixture, followed by 12.7 g of intermediate 1-b, added portion-wise. After overnight stirring at room temperature, the reaction mixture was washed with water, dried over MgSO$_4$, filtered and evaporated to yield 11 g (40%) of the desired intermediate 5-a, [5-[[[(2R,3S)-3-(dibenzylamino)-2-hydroxy-4-phenylbutyl](2-methylpropyl)amino]sulfonyl]-1H-benzimidazol-2-yl]carbamic acid, methyl ester.

11 g of intermediate 5-a were dissolved in 150 mL of dioxane. Then 18 g of Na$_2$CO$_3$ dissolved in 150 mL of water were added to the reaction mixture, which was stirred at 90° C. during 24 hours. The reaction mixture was then concentrated and the residue extracted with DCM, then ethylacetate. The residue was then dried by concentration with toluene, then mixed with isopropanol and filtered. The crystals were further dried in a vacuum oven at 50° C., to give 7.76 g (79%) of intermediate 5-b N-[(2R,3S)-3-(dibenzylamino)-2-hydroxy-4-phenylbutyl]-N-(2-methylpropyl)-[2-aminobenzimidazol-5-yl]sulfonamide.

3 g of intermediate 5-b and 0.76 mL triethylamine were mixed in 150 mL of THF, at 0° C. Then 0.39 g of acetylchloride dissolved in THF were added to the reaction mixture, which was stirred during 3 hours at room temperature. 0.7 g of 4-dimethyl-aminopyridine were added and the reaction stirred overnight. 0.39 g of acetylchloride and 0.7 g of 4-dimethylaminopyridine were then added to the reaction mixture which was further stirred until all intermediate 5-b has reacted. The reaction mixture was then washed with water and extracted with DCM. The organic layer was dried over MgSO$_4$, filtered and evaporated to yield 1.1 g (34%) of the desired intermediate 5-c N-[(2R,3S)-3-(dibenzylamino)-2-hydroxy-4-phenylbutyl]-N-(2-methylpropyl)[2-(acetylamino)-benzimidazol-5-yl]sulfonamide.

1.1 g of intermediate 5-c was dissolved in 200 mL of methanol. Then the reaction mixture was hydrogenated in the presence of 0.5 g of palladium on charcoal (10%), at room temperature, overnight. After filtration of the catalyst, the reaction mixture was hydrogenated again in the presence of newly added palladium on charcoal (10%). This step was again repeated twice then the reaction mixture was concentrated and the crude compound was purified on silica gel eluting with 2% methanol in DCM, yielding 0.2 g (25%) of the desired intermediate N-[(2R,3S)-3-amino-2-hydroxy-4-phenylbutyl]-N-(2-methylpropyl)[2-(acetylamino)benzimidazol-5-yl]sulfonamide (5-d).

200 mg of intermediate 5-d were dissolved in 2 mL of DCM, then 25 mg of 2,6-di-methylphenoxyacetic acid, 27 mg of EDCI and 19 mg of HOBt were added to the reaction mixture, which was stirred at room temperature overnight then evaporated. The crude compound was purified by preparative HPLC, yielding 27 mg (30%) of the final compound [(1S,2R)-3-[[[2-(acetylamino)benzimidazol-5-yl]sulfonyl](2-methyl-propyl)amino]-2-hydroxy-1-(phenylmethyl)propyl]-(2,6-dimethyl phenoxy)acetamide (compound 9).

EXAMPLE 6

Preparation of Compound 64

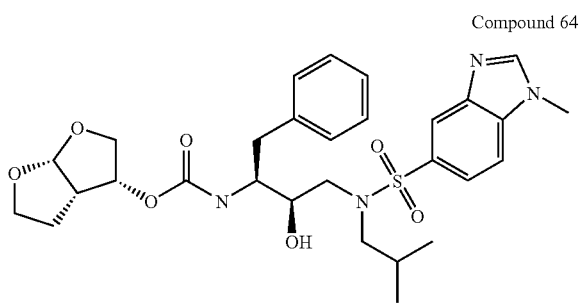

Compound 64

A mixture of 34.20 g of intermediate C-1 (PG=dibenzyl, $R_4$=isobutyl) and 12.48 g of triethylamine in 250 ml of dichloromethane was stirred at 0° C. Then 25.16 g of intermediate A-4 was added and the reaction was stirred at room temperature. After 1 hour an extra 3 g of intermediate A-4 was added and the reaction was stirred during weekend. After washing with 5% HCl solution, saturated NaHCO$_3$ solution and brine, the organic layer was separated, dried and evaporated to give the intermediate 6-a N-[(2R,3S)-3-(dibenzylamino)-2-hydroxy-4-phenylbutyl]-N-(2-methylpropyl)(4-chloro-3-nitrophenyl)sulfonamide which was used in the next step without further purification.

A mixture of 11.75 g of intermediate 6-a and 12 ml of methylamine (40 wt % in H$_2$O) in 100 ml of methanol was stirred at room temperature for 24 hours. After evaporation under reduced pressure, the product was washed with H$_2$O and extracted with EtOAc. The organic layer was dried and evaporated under reduced pressure to give the intermediate 6-b N-[(2R,3S)-3-(dibenzylamino)-2-hydroxy-4-phenylbutyl]-N-(2-methylpropyl)(4-methylamino-3-nitrophenyl)sulfonamide which was used in the next step without further purification.

A mixture of 11.5 g of intermediate 6-b, 2 ml of thiophene in diisopropylether (4%) and 1 g of palladium on charcoal (10%) in 100 ml of methanol was hydrogenated. After filtering over decalite, the filtrate was evaporated under reduced pressure to give the intermediate 6-c N-[(2R,3S)-3-(dibenzylamino)-2-hydroxy-4-phenylbutyl]-N-(2-methylpropyl)(3-amino-4-methylaminophenyl)sulfonamide which was used in the next step without further purification.

A mixture of 2 g of intermediate 6-c and 0.23 g of formic acid was stirred in 100 ml of dioxane/100 ml of 5N HCl for 48 hours at 110° C. After cooling, EtOAc was added and the reaction was poured onto a mixture of ice, saturated NaHCO$_3$ solution and EtOAc. After extraction with EtOAc, the organic layer was dried and evaporated under reduced pressure. The crude product was purified on silica gel eluting with 1% of methanol in dichloromethane to give 2.23 g of intermediate 6-d N-[(2R,3S)-3-(dibenzylamino)-2-hydroxy-4-phenylbutyl]-N-(2-methylpropyl)(1,2-dimethyl benzimidazol-5-yl)-sulfonamide.

A mixture of 2.23 g of intermediate 6-d, 1.38 g of ammonium formate and 1.2 g of palladium on charcoal (10%) in 50 ml of ethanol was stirred at 80° C. for 1.5 hours. After filtering over decalite, the filtrate was evaporated under reduced pressure. The residue was purified by preparative HPLC to give 0.29 g of intermediate 6-e N-[(2R,3S)-3-amino-2-hydroxy-4-phenylbutyl]-N-(2-methylpropyl)(1-methyl benzimidazol-5-yl)sulfonamide, with a yield of 18%.

A mixture of 0.35 g of intermediate 6-e, 0.22 g of 1-[[(3R,3aS,6aR)-hexahydrofuro-[2,3-b]furan-3-yl]oxycarbonyloxy]-2,5-pyrrolidinedione and 0.12 g of triethylamine in 20 ml of dichloromethane was stirred at room temperature for 48 hours. After washing with saturated NaHCO$_3$ solution, the organic layer was dried and evaporated under reduced pressure. The residue was purified by preparative HPLC to give 0.105 g of the final compound [(1S,2R)-3-[[(1-methylbenzimidazol-5-yl)sulfonyl](2-methyl-propyl)amino]-2-hydroxy-1-(phenylmethyl)propyl]carbamic acid, [(3R,3aS,6aR)-hexahydrofuro[2,3-b]furan-3-yl]ester, with a yield of 22% (compound 64).

EXAMPLE 7

Preparation of Compound 24

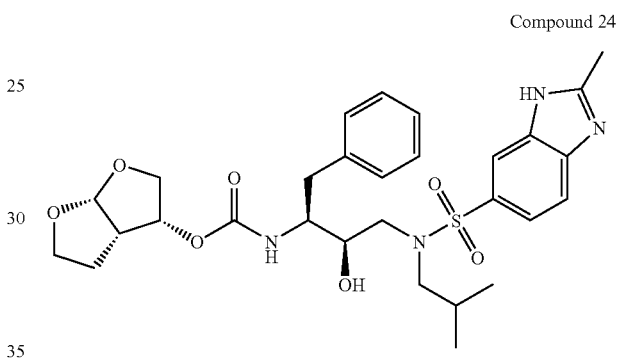

Compound 24

20 g of intermediate D-4 (PG=dibenzyl, $R_4$=isobutyl) in 400 ml of ammonia in isopropanol was stirred at 120° C. overnight. After evaporation under reduced pressure, the product was washed with H$_2$O and extracted with dichloromethane. The organic layer was dried and evaporated under reduced pressure to give the intermediate 7-a N-[(2R,3S)-3-(dibenzylamino)-2-hydroxy-4-phenylbutyl]-N-(2-methylpropyl)(4-amino-3-nitrophenyl)sulfonamide which was used in the next step without further purification.

A mixture of 20 g of intermediate 7-a, 3 ml of thiophene in diisopropylether (4%) and 2 g of palladium on charcoal (10%) in 150 ml of methanol was hydrogenated. After filtering over decalite, the filtrate was evaporated under reduced pressure to give the intermediate 7-b N-[(2R,3S)-3-(dibenzylamino)-2-hydroxy-4-phenylbutyl]-N-(2-methylpropyl)(3,4-diaminophenyl)sulfonamide which was used in the next step without further purification.

A mixture of 1 g of intermediate 7-b and 0.13 g of acetic acid was stirred in 40 ml of dioxane/40 ml of 5N HCl for 48 hours at 110° C. After cooling, EtOAc was added and the reaction was poured onto a mixture of ice, saturated NaHCO$_3$ solution and EtOAc. After extraction with EtOAc, the organic layer was dried and evaporated under reduced pressure to give the intermediate 7-c N-[(2R,3S)-3-(dibenzylamino)-2-hydroxy-4-phenylbutyl]-N-(2-methylpropyl)(2-methylbenzimidazol-5-yl)sulfonamide which was used in the next step without further purification.

A mixture of 1.55 g of intermediate 7-c and 0.4 g of palladium on charcoal (10%) in 20 ml of methanol was hydrogenated. After filtering over decalite, the filtrate was evaporated under reduced pressure. The crude compound was purified on silica gel eluting with 4% of methanol in dichloromethane to give 0.18 g of intermediate 7-d N-[(2R,3S)-3-amino-2-hydroxy-4-phenylbutyl]-N-(2-methylpropyl)(2-methyl-benzimidazol-5-yl)sulfonamide.

A mixture of 0.18 g of intermediate 7-d, 0.11 g of 1-[[(3R,3aS,6aR)-hexahydrofuro-[2,3-b]furan-3-yl]oxycarbonyloxy]-2,5-pyrrolidinedione and 46 mg of triethylamine in ml of dichloromethane was stirred at room temperature for 17 hours. After washing with saturated NaHCO$_3$ solution, the organic layer was dried and evaporated under reduced pressure. The residue was purified on silica gel eluting with 2% of methanol in dichloromethane to give 0.22 g of the final compound [(1S,2R)-2-hydroxy-3-[[(2-methylbenzimidazol-5-yl)sulfonyl](2-methylpropyl)amino]-1-(phenylmethyl)propyl]-carbamic acid, [(3R,3aS,6aR)-hexahydrofuro[2,3-b]furan-3-yl]ester with a yield of 89% (compound 24).

EXAMPLE 8

Preparation of Compound 20

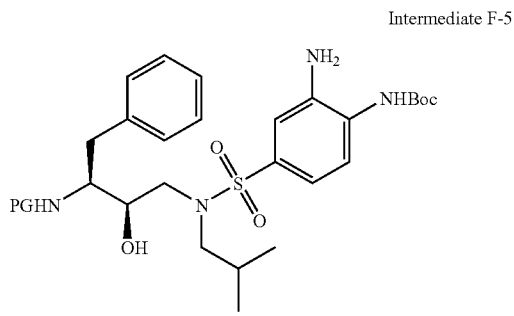

Intermediate F-5

37 g of intermediate F-5 (PG=dibenzyl, PG'=boc, R$_4$=isobutyl) and 6.5 g of triethylamine were mixed in 100 mL of DCM. 26.2 g of Boc$_2$O were then added at 0° C., then the reaction mixture was heated at 50° C. during 2 days and evaporated to give 49 g of the desired intermediate 8-a [4-[[[(2R,3S)-3-(dibenzylamino)-2-hydroxy-4-phenylbutyl](2-methylpropyl)amino]sulfonyl]-2-nitrophenyl]carbamic acid, 1,1-dimethylethyl ester, used without further purification in the next step.

42 g of 8-a were dissolved in 500 mL of methanol and hydrogenated in the presence of palladium on charcoal (10%) and thiophene. The reaction mixture was then evaporated and purified on silica gel eluting with DCM, yielding 30 g (75%) of intermediate 8-b [2-amino-4-[[[(2R,3S)-3-(dibenzylamino)-2-hydroxy-4-phenylbutyl](2-methylpropyl)amino]sulfonyl]phenyl]carbamic acid, 1,1-dimethylethyl ester.

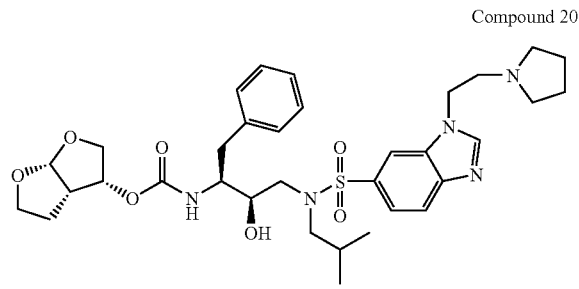

Compound 20

1.44 g of intermediate 8-b, 284 mg of chloroacetyl chloride and 262 mg of triethyl-amine were mixed in 20 mL of DCM at 0° C. The reaction mixture was then stirred at room temperature overnight, then washed with water, dried over MgSO$_4$ and evaporated to yield 1.5 g of intermediate 8-c [2-(chloroacetylamino)-4-[[[(2R,3S)-3-(dibenzylamino)-2-hydroxy-4-phenylbutyl](2-methylpropyl)amino]sulfonyl]phenyl]carbamic acid, 1,1-dimethylethyl ester, used without further purification in the next step.

800 mg of 8-c and 298 mg of pyrrolidine were mixed in 10 mL of THF. The reaction mixture was stirred at room temperature overnight and evaporated. The residue was treated with a mixture of water and DCM. The organic phase was dried over MgSO$_4$ and evaporated to yield 920 mg of intermediate 8-d [4-[[[(2R,3S)-3-(dibenzylamino)-2-hydroxy-4-phenylbutyl](2-methylpropyl)amino]sulfonyl]-2-[[(pyrrolidin-1-yl)acetyl]-amino]phenyl]carbamic acid, 1,1-dimethylethyl ester, used without further purification in the next step.

920 mg of the previous intermediate 8-d and 1.3 g of acid trifluoroacetic were mixed in mL of DCM. The reaction mixture was stirred at room temperature overnight, then a saturated solution of NaHCO$_3$ in water was added. The organic layer was separated and evaporated to yield 790 mg of intermediate 8-e [2-amino-5-[[[(2R,3S)-3-(dibenzyl-amino)-2-hydroxy-4-phenylbutyl](2-methylpropyl)amino]sulfonyl]phenyl]-(pyrrolidin-1-yl)acetamide, used without further purification in the next step.

790 mg of the previous intermediate 8-e was dissolved in 10 mL of THF. 129 mg of LiAlH$_4$ was then added and the reaction mixture was stirred at reflux during 3 hours. 2 mL of water and 2 mL of a 20% solution of NaOH in water were then added to the reaction mixture, which was filtered over decalite and evaporated to yield 780 mg of intermediate 8-f N-[(2R,3S)-3-(dibenzylamino)-2-hydroxy-4-phenylbutyl]-N-(2-methylpropyl)[4-amino-3-[2-(pyrrolidin-1-yl)ethylamino]phenyl]sulfonamide, used without further purification in the next step.

780 mg of the previous intermediate 8-f and 30 mL of HCl 5N in isopropanol were mixed in 30 mL of dioxane. 2 mL of formic acid were then added and the reaction mixture stirred at 100° C. during 4 hours. After cooling to room temperature, EtOAc was added and, while maintaining a vigourous stirring, solid K$_2$CO$_3$ was added to neutralize the reaction mixture. The organic layer was then separated and evaporated to yield 850 mg of intermediate 8-g N-[(2R,3S)-3-(dibenzylamino)-2-hydroxy-4-phenylbutyl]-N-(2-methylpropyl)[1-[2-(pyrrolidin-1-yl)ethyl]benzimidazol-6-yl]sulfonamide, used without further purification in the next step.

850 mg of the previous intermediate 8-g, ammonium formate and palladium on charcoal (10%) were mixed in 10 mL of ethanol. The reaction mixture was heated at 80° C. and stirred during 2 hours, then filtered on decalite and purified on silica gel, yielding 320 mg of the deprotected compound 8-b N-[(2R,3S)-3-amino-2-hydroxy-4-phenylbutyl]-N-(2-methylpropyl)[1-[2-(pyrrolidin-1-yl)ethyl]benzimidazol-6-yl]-sulfonamide.

320 mg of the previous intermediate 8-h, 169 mg of 1-[[(3R,3aS,6aR)-hexahydrofuro-[2,3-b]furan-3-yl]oxycarbonyloxy]-2,5-pyrrolidinedione and 70 mg of triethylamine were mixed in 10 mL of DCM. The reaction mixture was stirred at room temperature for 4 hours, evaporated and purified on silica gel eluting with 8% ammonia in DCM, yielding 112 mg (27%) of the desired final compound [(1S,2R)-2-hydroxy-1-(phenyl-methyl)-3-[[[1-[2-(pyrrolidin-1-yl)ethyl]benzimidazol-6-yl]sulfonyl](2-methylpropyl)-amino]propyl]carbamic acid, [(3R,3aS,6aR)-hexahydro furo[2,3-b]furan-3-yl]ester (compound 25).

EXAMPLE 9

Preparation of Compound 40

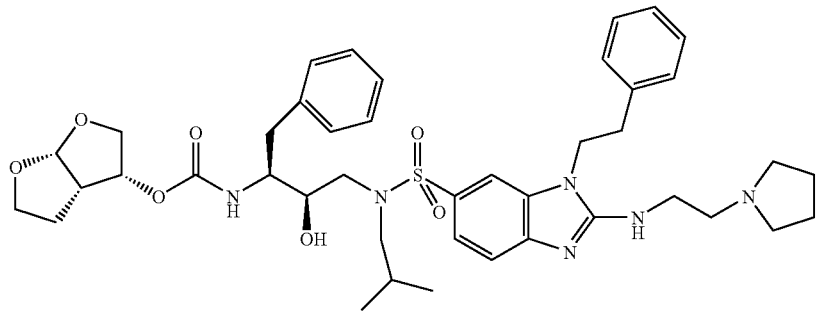

To 1.5 g of intermediate F-5 (PG, PG'=Boc, $R_4$ isobutyl) dissolved in 25 mL of DCM, were added 321 μL of phenylacetaldehyde and 1.06 g of sodium triacetoxyboro-hydride. The mixture was stirred at room temperature overnight, then washed with a saturated solution of $Na_2CO_3$ in water, then brine, dried over $MgSO_4$ and evaporated to give 2.1 g (100%) of intermediate H-5' (=H-5 wherein PG, PG'=boc, $R_4$=isobutyl, $R_{13}$ is phenylethyl) as an orange oil.

2.1 g of intermediate H-5' were dissolved in 50 mL of dioxane and reacted with 100 mL of HCl 7N in isopropanol, at room temperature, for 16 hours. The reaction mixture was then evaporated and treated with a mixture of DCM and a saturated solution of $Na_2CO_3$ in water, dried over $MgSO_4$ and evaporated to give 1.4 g of crude intermediate which was used directly in the next step.

1.4 g of the previous intermediate, 677 mg of 1-[[(3R,3aS, 6aR)-hexahydrofuro-[2,3-b]furan-3-yl]oxycarbonyloxy]-2, 5-pyrrolidinedione and 250 mg of triethylamine were mixed in 25 mL of DCM. The reaction mixture was stirred at room temperature for 2 hours, evaporated and purified on silica gel eluting with 5% methanol in DCM, yielding 900 mg (56%) of the desired compound I-7' (=I-7 wherein $R_{13}$ is phenyl-ethyl, $R_1$-L is 1-[[(3R,3aS,6aR)-hexahydrofuro[2,3-b]furan-3-yl] oxycarbonyl], $R_4$ is isobutyl).

800 mg of intermediate I-7' and 428 mg of thiocarbonyl diimidazole were dissolved in 10 mL of THF. After stirring at room temperature for 16 hours, 215 mg of thiocarbonyl diimidazole were added to the mixture. After 16 hours, the reaction mixture was evaporated and purified on silica gel eluting with 5% methanol in DCM, yielding 350 mg (41%) of the desired compound J-7' (=J-7 wherein $R_{13}$ is phenylethyl, $R_1$-L is 1-[[(3R,3aS,6aR)-hexahydrofuro[2,3-b]furan-3-yl]oxycarbonyl], $R_4$ is isobutyl)

To 350 mg of intermediate J-7' were added 31 μL of MeI and 69 mg of $K_2CO_3$ in 5 mL of DMF. The mixture was stirred at room temperature for 1 hour, then evaporated, dissolved in DCM and washed with brine, dried over $MgSO_4$ and evaporated to yield 360 mg (100%) of intermediate K-7' (=K-7 wherein $R_{13}$ is phenylethyl, $R_1$-L is 1-[[(3R,3aS,6aR)-hexahydrofuro[2,3-b]furan-3-yl]oxycarbonyl], $R_4$ is isobutyl, R is methyl) which was used without further purification in the next step.

360 mg of intermediate K-7' and 122 mg of mCPBA were dissolved in 5 mL of DCM and stirred at room temperature for 2 hours. 100 mg of mCPBA were then added to the mixture which was stirred for another hour, then washed with a saturated solution of $Na_2CO_3$ in water, then brine, dried over $MgSO_4$ and purified on silica gel eluting with 1% methanol in DCM, yielding 140 mg (38%) of the desired intermediate L-7' (=L-7 wherein $R_{13}$ is phenylethyl, $R_1$-L is 1-[[(3R,3aS,6aR)-hexahydrofuro[2,3-b]-furan-3-yl]oxycarbonyl], $R_4$ is isobutyl).

To 140 mg of intermediate L-7' dissolved in 10 mL of acetonitrile were added 1 mL of 1-(2-Aminoethyl)pyrrolidine. The reaction mixture was stirred 48 hours under reflux, then evaporated and purified by preparative HPLC, yielding 60 mg (40%) of the desired final compound 40 [(1S,2R)-2-hydroxy-3-[[[[1-(phenethyl)-2-[2-(pyrrolidin-1-yl)ethylamino]]benzimidazol-6-yl]sulfonyl](2-methylpropyl) amino]-1-(phenylmethyl)propyl]carbamic acid, [(3R,3aS, 6aR)-hexahydrofuro[2,3-b]furan-3-yl]ester. Mass spectral data: m/z=789 (M+H).

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

An interesting group of intermediates are those intermediates wherein -A-$R_6$ is hydrogen. Said intermediates may also have pharmacological properties similar to those pharmacological properties of the compounds of formula (I).

The present compounds can thus be used in animals, preferably in mammals, and in particular in humans as pharmaceuticals per se, in mixtures with one another or in the form of pharmaceutical preparations.

Furthermore, the present invention relates to pharmaceutical preparations which as active constituents contain an effective dose of at least one of the compounds of formula (I) in addition to customary pharmaceutically innocuous excipients and auxiliaries. The pharmaceutical preparations normally contain 0.1 to 90% by weight of a compound of formula (I). The pharmaceutical preparations can be prepared in a manner known per se to one of skill in the art. For this purpose, at least one of a compound of formula (I), together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention can be administered orally using e.g. including suspensions, capsules, tablets, sachets, solutions, suspensions, emulsions; parenterally, using e.g subcutaneous, intravenous, intramuscular, intrasternal injection or infusion techniques; rectally using e.g. suppositories; intravaginally; by inhalation, or topically, the preferred administration being dependent on the individual case, e.g., the particular course of the disorder to be treated. Oral administration is preferred.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Due to their favorable pharmacological properties, particularly their activity against multi-drug resistant HIV protease enzymes, the compounds of the present invention are useful in the treatment of individuals infected by HIV and for the prophylaxis of these individuals.

The prophylaxis treatment can be advantageous in cases where an individual has been subjected to a high risk of exposure to a virus, as can occur when individual has been in contact with an infected individual where there is a high risk of viral transmission. As an example, prophylactic administration of said compounds would be advantageous in a situation where a health care worker has been exposed to blood from an HIV-infected individual, or in other situations where an individual engaged in high-risk activities that potentially expose that individual to the HIV virus.

In general, the compounds of the present invention may be useful in the treatment of warm-blooded animals infected with viruses whose existence is mediated by, or depends upon, the protease enzyme. Conditions which may be prevented or treated with the compounds of the present invention include, but is not limited to, treating a wide range of states of HIV infection: AIDS, ARC (Aids related complex), both symptomatic and asymptomatic, and actual or potential exposure to HIV. The compounds of the present are also useful for treating progressive generalized lymphadenophaty, Kaposi's syndrome, thrombocytopenia purpurea, AIDS-related neurological conditions such as AIDS dementia complex, multiple sclerosis, tropical parapesis, and also anti-HIV antibody positive and HIV-positive conditions, including such conditions in asymptomatic patients. For example, the compounds of this invention are useful in treating infection by HIV after suspected past exposure to HIV by e.g., blood transfusion, exchange of body fluids, bites, accidental needle stick, or exposure to patient blood during surgery. The term prevention includes prophylaxis of HIV infection and prophylaxis of the evolution of HIV infection to AIDS.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1. Consequently, the compounds of the present invention can be used in the manufacture of a medicament useful for treating conditions associated with HIV and other pathogenic retroviruses, in particular medicaments useful for treating patients infected with multi-drug resistant HIV virus.

In a preferred embodiment, the invention relates to the use of a compound of formula (I) or any subgroup thereof in the manufacture of a medicament for treating or combating infection or disease associated with multi-drug resistant retrovirus infection in a mammal, in particular HIV-1 infection. Thus, the invention also relates to a method of treating a retroviral infection, or a disease associated with multi-drug resistant retrovirus infection comprising administering to a mammal in need thereof an effective amount of a compound of formula (I) or a subgroup thereof.

In another preferred embodiment, the present invention relates to the use of formula (I) or any subgroup thereof in the manufacture of a medicament for inhibiting a protease of a multi-drug resistant retrovirus in a mammal infected with said retrovirus, in particular HIV-1 retrovirus.

In another preferred embodiment, the present invention relates to the use of formula (I) or any subgroup thereof in the manufacture of a medicament for inhibiting multi-drug resistant retroviral replication, in particular HIV-1 replication.

An advantage of the compounds of the present invention is that the compounds display activity towards HIV strains carrying mutations in the protease gene. It is known in the art that mutants of the HIV protease confer resistance to HIV protease inhibitors. Examples of such mutations comprise those mutations, independently selected from the list comprising mutations at amino acid positions 3, 10, 11, 13, 15, 19, 20, 22, 24, 30, 32, 33, 35, 36, 37, 41, 43, 46, 47, 48, 50, 53, 54, 55, 57, 58, 62, 63, 66, 70, 71, 72, 73, 77, 82, 84, 85, 88, 89 or 90 in the HIV protease. The compounds of the present invention may be useful to prevent or delay the onset of mutations in HIV protease, or if the HIV protease contains mutations at the initiation of therapy may prevent or delay the occurrence of additional mutations in the HIV protease.

The compounds of the present invention may also find use in inhibiting ex vivo samples containing HIV or expected to be exposed to HIV. Hence, the present compounds may be used to inhibit HIV present in a body fluid sample which contains or is suspected to contain or be exposed to HIV.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4, PRO-542, BMS-806; fusion inhibitors, such as, for example, T20, T1249, RPR 103611, YK-FH312, IC 9564, 5-helix, D-peptide ADS-J1; co-receptor binding inhibitors, such as, for example, AMD 3100, AMD-3465, AMD7049, AMD3451 (Bicyclams), TAK220, TAK 779, T-22, ALX40-4C; SHC-C (SCH351125), SHC-D, PRO-140, RPR103611, AK-602; RT inhibitors, such as, for example, foscarnet and prodrugs; nucleoside RTIs, such as, for example, AZT, 3TC, DDC, DDI, D4T, Abacavir, FTC, DAPD (Amdoxovir), dOTC (BCH-10652), fozivudine, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC-442, UC 781, UC 782, Capravirine, QM96521, GW420867X, GW-3011, GW-4511, GW-4751, DPC 961, DPC963, DPC082, DPC083, TMC-125, calanolide A, SJ-3366, TSAO, 4"-deaminated TSAO, MV150, MV026048, PNU-142721; RNAse H inhibitors, such as, for example, SP1093V, PD126338; TAT inhibitors, such as, for example, RO-5-3335, K12, K37; integrase inhibitors, such as, for example, L 708906, L 731988, S-1360; protease inhibitors, such as, for example, amprenavir and prodrug GW908, ritonavir, nelfinavir, saquinavir, indinavir, lopinavir, palinavir, BMS 186316, atazanavir, DPC 681, DPC 684, tipranavir, AG1776, mozenavir, DMP-323, GS3333, KNI-413, KNI-272, L754394, L756425, LG-71350, PD161374, PD173606, PD177298, PD178390, PD178392, PNU 140135, TMC-114, maslinic acid, U-140690, RO-033-4649; glycosylation inhibitors, such as, for example, castanospermine, deoxynojirimycine; entry inhibitors CGP64222.

The compounds of the present invention may also be administered in combination with immunomodulators e.g., bropirimine, anti-human alpha interferon antibody, IL-2, methionine enkephalin, interferon alpha, and naltrexone; with antibiotics e.g., pentamidine isothiorate; cytokines (e.g. Th2); modulators of cytokines; chemokines or the receptors thereof (e.g. CCR5); or hormones (e.g. growth hormone) or the receptors thereof; to ameliorate, combat, or eliminate HIV infection and its symptoms. Such combination therapy in different formulations, may be administered simultaneously, sequentially or independently of each other. Alternatively, such combination may be administered as a single formulation, whereby the active ingredients are released from the formulation simultaneously or separately.

The compounds of the present invention may also be administered in combination with modulators of the metabolization following application of the drug to an individual. These modulators include compounds that interfere with the metabolization at cyto-chromes, such as cytochrome P450. Some modulators inhibit cytochrome P450. It is known that several isoenzymes exist of cytochrome P450, one of which is cytochrome P450 3A4. Ritonavir is an example of a modulator of metabolization via cytochrome P450. Interesting compounds having an effect at cytochrome P450 include those compounds containing a thiazolyl, imidazolyl or pyridinyl moiety. Such combination therapy in different formulations, may be administered simultaneously, separately or sequentially. Alternatively, such combination may be administered as a single formulation, whereby the active ingredients are released from the formulation simultaneously or separately.

Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

The combination may provide a synergistic effect, whereby viral infectivity and its associated symptoms may be prevented, substantially reduced, or eliminated completely. Combinations of the compounds of formula (I) with another HIV protease inhibitor as cytochrome $P_{450}$ inhibitor can act synergistically, in an additive way or antagonistically. This can be assessed in an experimental setting where the potency of different ratios of the two HIV-protease inhibitors is measured. Results can be plotted in an isobologram graph according to the method described by Chou and Talalay (Adv. Enzyme Regul. 22: 27-55, 1984) Synergism between two inhibitors would mean a more potent combination therapy, but with no increase in undesired side effects.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions; or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds of formula (I) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ α-, β- or γ-cyclo-dextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxy-ethyl, hydroxypropyl or hydroxybutyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$ alkyloxy$C_{1-6}$alkyl, particularly carboxymethoxypropyl or carboxyethoxy-propyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavors.

Other convenient ways to enhance the solubility of the compounds of the present invention in pharmaceutical compositions are described in WO-94/05263, WO98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present compounds are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

Another aspect of the present invention concerns a kit or container comprising a compound of formula (I) in an amount effective for use as a standard or reagent in a test or assay for determining the ability of a potential pharmaceutical to inhibit HIV protease, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram™. The Antivirogram™ is a highly automated, high throughput, second generation, recombinant assay that can measure susceptibility, especially viral susceptibility, to the compounds of the present invention. (Hertogs K, de Bethune M P, Miller V et al. *Antimicrob Agents Chemother,* 1998; 42(2):269-276, incorporated by reference).

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight and individual responsiveness of the human or animal to be treated and on whether the therapy is acute or prophylactic. Customarily, the daily dose of a compound of formula (I) in the case of administration to a patient approximately 75 kg in weight is 0.1 mg to 10 g, preferably 1 mg to 1 g, more preferably 3 mg to 0.5 g. The dose can be administered in the form of an individual dose, or divided into several, e.g. two, three, or four, individual doses.

The following tables list the compounds of formula (I) which were prepared following one of the above reaction schemes. ND means not determined.

TABLE 1

| No | R | R12 | R13 | pIC₅₀ (LAI) |
|---|---|---|---|---|
| 1 | (hexahydrofuro[2,3-b]furan-3-yl acetate) | H | –CH₂–C₆H₅ | 9.1 |
| 2 | (hexahydrofuro[2,3-b]furan-3-yl acetate) | –CH₃ | –CH₂–C₆H₅ | 9.0 |
| 3 | (hexahydrofuro[2,3-b]furan-3-yl acetate) | –H | –CH₂–CH(CH₃)₂ | 8.7 |
| 4 | (hexahydrofuro[2,3-b]furan-3-yl acetate) | –H | –CH₂–C₆H₅ | 8.7 |
| 5 | (hexahydrofuro[2,3-b]furan-3-yl acetate) | –H | –CH₂–CH₂–C₆H₅ | 8.7 |
| 6 | 2,6-dimethylphenoxy-CH₂-C(=O)- | –NHCOOCH₃ | –H | 8.6 |
| 7 | (hexahydrofuro[2,3-b]furan-3-yl acetate) | –H | –CH₂–CH(CH₃)–CH₃ | 8.6 |
| 8 | 2,6-dimethylphenoxy-CH₂-C(=O)- | –NHCOOCH₃ | –H | 8.5 |

TABLE 1-continued
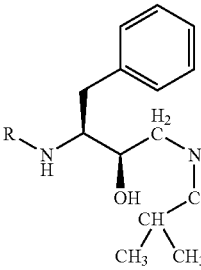
| No | R | R12 | R13 | pIC$_{50}$ (LAI) |
|---|---|---|---|---|
| 9 | 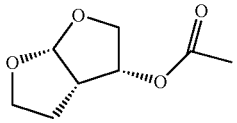 | —NHCOCH$_3$ | —H | 8.4 |
| 10 | 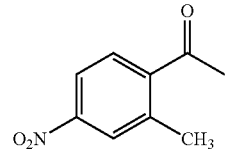 | —NHCOOCH$_3$ | —H | 8.0 |
| 11 | 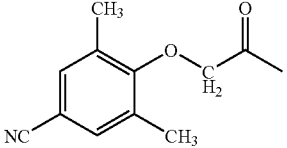 | —NHCOOCH$_3$ | —H | 8.0 |
| 12 | 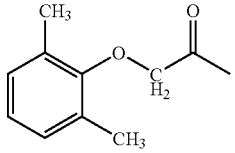 | —NHCOOCH$_3$ | —H | 7.8 |
| 13 | 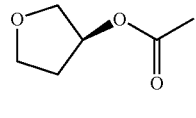 | —NH$_2$ | —CH$_3$ | 7.7 |
| 14 | 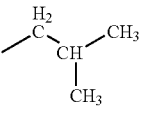 | —H | 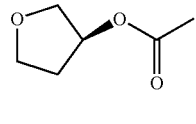 | 7.7 |
| 15 | 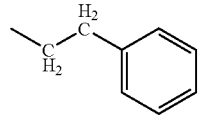 | —H | 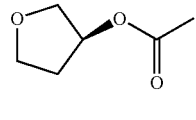 | 7.7 |
| 16 |  | —H | —CH$_3$ | 7.7 |

TABLE 1-continued

| No | R | R12 | R13 | pIC$_{50}$ (LAI) |
|---|---|---|---|---|
| 17 | hexahydrofuro[2,3-b]furan-3-yl acetate | —NHCOOCH$_3$ | —H | 7.6 |
| 18 | hexahydrofuro[2,3-b]furan-3-yl acetate | —H | —CH$_3$ | ND |
| 19 | 4-(dimethylamino)-2,6-dimethylphenoxyacetone | —NHCOOCH$_3$ | —H | 7.5 |
| 20 | hexahydrofuro[2,3-b]furan-3-yl acetate | —H | —CH$_2$CH$_2$-pyrrolidine | 7.4 |
| 21 | hexahydrofuro[2,3-b]furan-3-yl acetate | —H | —CH$_2$CH$_2$-(2-pyridyl) | 7.4 |
| 22 | 4-amino-2-methylacetophenone | —NHCOOCH$_3$ | —H | 7.4 |
| 23 | thiazol-5-ylmethyl acetate | —H | —H | 7.3 |
| 24 | hexahydrofuro[2,3-b]furan-3-yl acetate | —CH$_3$ | —H | 7.3 |

TABLE 1-continued

| No | R | R12 | R13 | pIC$_{50}$ (LAI) |
|---|---|---|---|---|
| 25 | 4-hydroxy-2-methylphenyl ketone | —NHCOOCH$_3$ | —H | 7.1 |
| 26 | 4-(aminomethyl)-2,6-dimethylphenoxy acetone | —NHCOOCH$_3$ | —H | 7.0 |
| 27 | (S)-tetrahydrofuran-3-yl acetate | —NHCOCH$_3$ | —H | 7.3 |
| 28 | hexahydrofuro[2,3-b]furan-3-yl acetate | —H | 4-pyridylmethyl | 7.5 |
| 29 | 2,6-dimethylphenoxy acetone | —H | —H | 7.1 |
| 30 | thiazol-5-ylmethyl acetate | —H | benzyl | 7.1 |
| 31 | 2,6-dimethylphenoxy acetone | —H | —CH$_3$ | 7.2 |
| 32 | thiazol-5-ylmethyl acetate | —H | isobutyl | 7.4 |

TABLE 1-continued
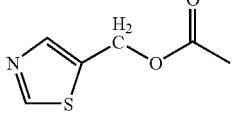
| No | R | R12 | R13 | pIC$_{50}$ (LAI) |
|---|---|---|---|---|
| 33 | 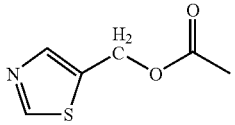 | —H | —CH$_3$ | 7.0 |
| 34 | 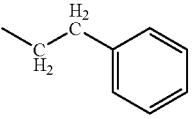 | —H | 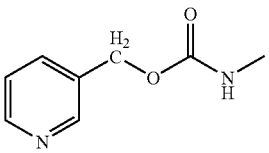 | 7.0 |
| 35 | 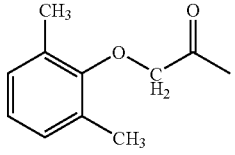 | —H | —H | 7.0 |
| 36 | 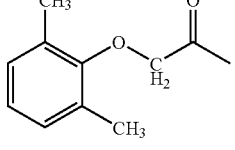 | —NH$_2$ | —H | 6.5 |
| 37 | 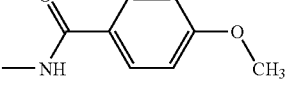 | 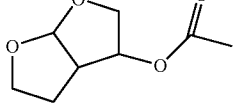 | —H | 6.9 |
| 38 | 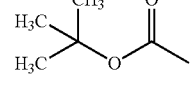 | —NHCOCH$_3$ | —H | 6.7 |
| 39 | 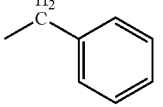 | —NH$_2$ | 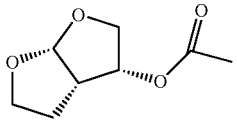 | 6.9 |
| 40 | 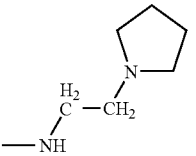 | 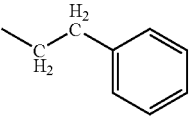 | 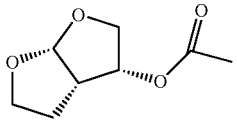 | 6.4 |

TABLE 1-continued

| No | R | R12 | R13 | pIC$_{50}$ (LAI) |
|---|---|---|---|---|
| 41 | (hexahydrofuro[2,3-b]furan-3-yl acetate) | —NH$_2$ | —CH$_3$ | 6.6 |
| 42 | (tetrahydrofuran-3-yl acetate) | —H | —H | 7.1 |
| 43 | (tert-butyl acetate) | —H | (phenethyl) | 6.4 |
| 44 | (hexahydrofuro[2,3-b]furan-3-yl acetate) | —H | (3-hydroxypropyl) | 6.1 |
| 45 | (2,6-dimethylphenoxyacetone) | —H | (isobutyl) | 6.3 |
| 46 | (3-amino-2-methylacetophenone) | —H | —H | 6.4 |
| 47 | (2,6-dimethylphenoxyacetone) | —H | (phenethyl) | 6.4 |
| 48 | (hexahydrofuro[2,3-b]furan-3-yl acetate) | (methyl N-[2-(dimethylamino)ethyl]carbamate) | —H | 6.4 |

TABLE 1-continued

| No | R | R12 | R13 | pIC$_{50}$ (LAI) |
|---|---|---|---|---|
| 49 | 5-methylisoxazol-3-yloxy-CH$_2$-C(=O)- | —H | —H | 6.3 |
| 50 | hexahydrofuro[2,3-b]furan-3-yl-O-C(=O)- | —H | —H | 6.9 |
| 51 | hexahydrofuro[2,3-b]furan-3-yl-O-C(=O)- | —H | —CH$_2$-(1-methyl-imidazol-5-yl) | 6.2 |
| 52 | tetrahydrofuran-3-yl-O-C(=O)- | CH$_3$NH-C(=O)-NH-CH$_2$-CH$_2$-N(CH$_3$)$_2$ | —H | 6.1 |
| 53 | tetrahydrofuran-3-yl-O-C(=O)- | —NH$_2$ | —H | 6.0 |
| 54 | pyridin-3-yl-CH$_2$-O-C(=O)-NH-CH$_3$ ? (pyridin-3-yl-CH$_2$-O-C(=O)-NHMe) | —NH$_2$ | —H | 5.8 |
| 55 | hexahydrofuro[2,3-b]furan-3-yl-O-C(=O)- | hexahydrofuro[2,3-b]furan-3-yl-O-C(=O)-O-CH$_2$- | —H | 5.8 |
| 56 | hexahydrofuro[2,3-b]furan-3-yl-O-C(=O)- | —CH$_2$OH | —H | 5.7 |
| 57 | thiazol-5-yl-CH$_2$-O-C(=O)- | —NH$_2$ | —H | 5.7 |

TABLE 1-continued
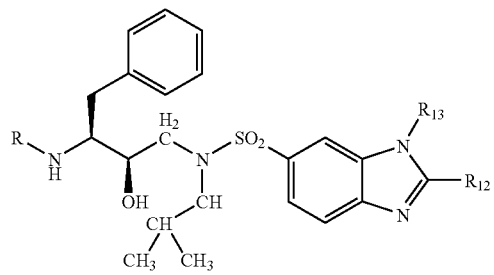
| No | R | R12 | R13 | pIC$_{50}$ (LAI) |
|----|---|-----|-----|------------------|
| 58 | 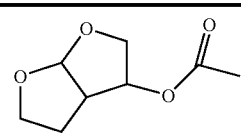 | 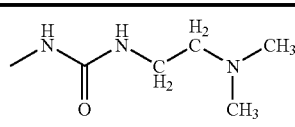 | —H | 5.6 |
| 59 | 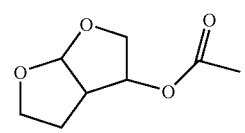 | —NH$_2$ | —H | 5.3 |
TABLE 2
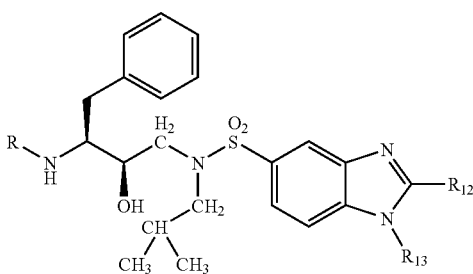
| No | R | R12 | R13 | pIC$_{50}$ (LAI) |
|----|---|-----|-----|------------------|
| 60 | 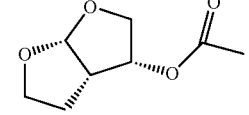 | —H | 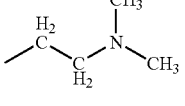 | 6.5 |
| 61 | 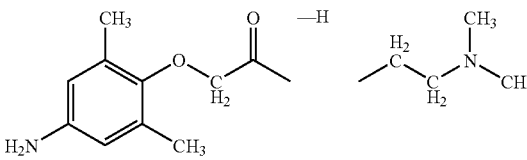 | —H | 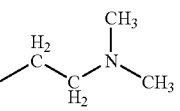 | 5.7 |
| 62 | 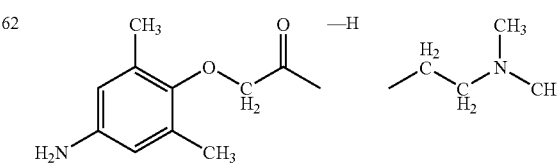 | —H | 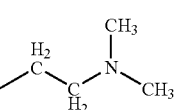 | 5.7 |

TABLE 2-continued

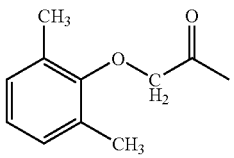

| No | R | R12 | R13 | pIC$_{50}$ (LAI) |
|---|---|---|---|---|
| 63 |  | —H | 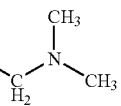 | ND |
| 64 | 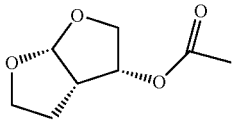 | —H | —CH$_3$ | 7.6 |

Antiviral Analyses:

The compounds of the present invention were examined for anti-viral activity in a cellular assay. The assay demonstrated that these compounds exhibited potent anti-HIV activity against a wild type laboratory HIV strain (HIV-1 strain LAI). The cellular assay was performed according to the following procedure.

HIV- or mock-infected MT4 cells were incubated for five days in the presence of various concentrations of the inhibitor. At the end of the incubation period, all HIV-infected cells have been killed by the replicating virus in the control cultures in the absence of any inhibitor. Cell viability is measured by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution is monitored at 540 nm. The values correlate directly to the number of living cells remaining in the culture at the completion of the five day incubation. The inhibitory activity of the compound was monitored on the virus-infected cells and was expressed as IC$_{50}$ and IC$_{90}$. These values represent the amount of the compound required to protect 50% and 90%, respectively, of the cells from the cytopathogenic effect of the virus. The toxicity of the compound was measured on the mock-infected cells and was expressed as CC$_{50}$, which represents the concentration of compound required to inhibit the growth of the cells by 50%. The selectivity index (SI) (ratio CC$_{50}$/IC$_{50}$) is an indication of the selectivity of the anti-HIV activity of the inhibitor. Wherever results are reported as e.g. pIC$_{50}$ or pCC$_{50}$ values, the result is expressed as the negative logarithm of the result expressed as IC$_{50}$ or CC$_{50}$ respectively.

Antiviral Spectrum:

Because of the increasing emergence of drug resistant HIV strains, the present compounds were tested for their potency against clinically isolated HIV strains harboring several mutations. These mutations are associated with resistance to protease inhibitors and result in viruses that show various degrees of phenotypic cross-resistance to the currently commercially available drugs such as for instance saquinavir, ritonavir, nelfinavir, indinavir and amprenavir. The viral strains R13025, R13027, R13028, R13029, R13034, R13080, T13127 and R13363 contained mutations as indicated below in Table 3.

TABLE 3

| List of mutations present in the protease gene of the HIV strains (A to H) used. | |
|---|---|
| A | V003I, L010I, V032T, L033M, E035D, S037Y, S037D, M046I, R057R/K, Q058E, L063P, K070T, A071V, I072V, I084V, L089V |
| B | V003I, L010I, K020R, E035D, M036I, S037D, Q058E, I062V, L063P, A071V, I072M, G073S, V077I, I084V, I085V, L090M |
| C | V003I, L010I, I015V, L019I, K020M, S037N, R041K, I054V, Q058E, L063P, A071V, I084V, L090M, I093L |
| D | V0031, L010L/1, I013V, L033I, E035D, M036I, M046L, K055R, R057K, L063P, I066F, A071V, I084V, N088D, L090M |
| E | V003I, L010I, V011I, A022V; L024I, E035D, M036I, S037T, R041K, I054V, I062V, L063P, A071V, I084V |
| F | L010F, M046I, M071V, I084V |
| G | V003I, L010I, VO32T, L033M, E035D, S037Y, M046I, I047V, R057R/K, Q058E, L063P, K070T, A071V, I072V, V082I, I084V, L089V |
| H | V003I, V0321, L035D, M036I, S037N, K043T, M046I, I047V, I050V, K055R, I057K, I062V, L063P, A071L, V082I, I085V, L090M, I093L |

Results:

As a measure of the broad spectrum activity of the present compounds, the fold resistance (FR), defined as FR=IC$_{50}$ (mutant strain)/IC$_{50}$(HIV-1 strain LAI), was determined. Table 4 shows the results of the antiviral testing in terms of fold resistance. As can be seen in this table, the present compounds are effective in inhibiting a broad range of mutant strains: Column A FR value towards mutant A; Column B: FR towards mutant B; Column C: FR towards mutant C; Column D: FR towards mutant D; Column E: FR towards mutant E; Column F: FR towards mutant F; Column G: FR towards mutant G; Column H: FR towards mutant H. The toxicity (column Tox) is expressed as the pCC$_{50}$ value as determined with mock transfected cells. Column WT displays the pIC50 value against wild type HIV-LAI strain.

TABLE 4

Results of the toxicity testing and the resistance testing against strain A to H (expressed as FR).

| N° | A | B | C | D | E | F | G | H | Tox | WT |
|---|---|---|---|---|---|---|---|---|---|---|
| 1 | 9.3 | 3.1 | 1.1 | 1.5 | 1.6 | 40 | 275 | 33 | 4.2 | 9.1 |
| 2 | 32 | 6.3 | 1.9 | 6.3 | 2.9 | 162 | ND | 89 | 4.2 | 9.0 |
| 3 | 15 | 2.7 | 1.0 | 1.2 | 0.9 | 83 | 112 | 20 | <4 | 8.7 |
| 4 | 18 | 3.4 | 2.0 | 3.0 | 2.2 | 48 | 224 | ND | 4.2 | 8.7 |
| 5 | ND | 1.9 | 0.9 | 1.9 | 3.2 | 78 | 110 | 49 | 4.1 | 8.7 |
| 6 | 2.9 | 2.0 | 2.7 | 2.1 | 1.6 | 10 | 60 | ND | <4 | 8.6 |
| 7 | ND | ND | 0.45 | 1.2 | 2.1 | 72 | 174 | ND | <4 | 8.6 |
| 8 | 2.1 | 2.0 | 1.4 | 1.9 | 2.3 | 16.2 | 89 | ND | <4 | 8.5 |
| 9 | 4.3 | 1.3 | 4.4 | 2.4 | 2.8 | 14 | 107 | ND | <4 | 8.4 |
| 11 | 5.4 | 1.0 | 1.5 | 3.5 | 1.6 | 7.1 | 245 | ND | <4 | 8.0 |
| 12 | 5.5 | 2.1 | 9.5 | 7.9 | 9.5 | 49 | 89 | ND | <4 | 7.8 |
| 13 | ND | 3.4 | 2.5 | 3.4 | 4.5 | ND | ND | ND | <4 | 7.7 |
| 15 | ND | 6.3 | 2.4 | 5.4 | 6.2 | 269 | 407 | ND | 4.2 | 7.7 |
| 16 | ND | ND | 2.6 | 5.9 | 5.4 | 288 | ND | ND | <4.49 | 7.7 |
| 17 | 0.69 | 1.1 | 1.0 | ND | 0.57 | 1.3 | 5.0 | ND | 4.1 | 7.6 |
| 19 | 5.6 | 1.2 | 1.4 | 3.6 | 3.5 | 83 | ND | ND | <4 | 7.5 |
| 21 | 14 | 1.1 | 0.83 | 1.1 | 1.1 | 25 | 83 | ND | <4 | 7.4 |
| 22 | 0.74 | 0.78 | 1.1 | 0.71 | 0.72 | 0.69 | 4.3 | ND | 4.1 | 7.4 |
| 23 | 7.1 | 2.3 | 3.5 | 2.5 | 4.8 | 23 | ND | ND | <4 | 7.3 |
| 24 | 2.6 | 0.85 | 1.1 | 0.89 | 0.83 | 4.7 | 35 | ND | <4 | 7.3 |
| 25 | 1.2 | ND | ND | ND | 1.3 | ND | ND | 4.6 | 4.3 | 7.1 |
| 26 | 6.3 | ND | ND | ND | 6.8 | ND | ND | 47 | 4.86 | 7.0 |
| 27 | 2.7 | ND | ND | ND | 1.1 | ND | ND | 2.3 | <4 | 7.3 |
| 28 | 1.5 | ND | ND | ND | 1.3 | ND | ND | 2.6 | ND | 7.5 |
| 29 | 14 | ND | ND | ND | 13 | ND | ND | 78 | 4.21 | 7.1 |
| 30 | 18 | ND | ND | ND | 13 | ND | ND | 65 | <4 | 7.1 |
| 31 | 13 | ND | ND | ND | 9.5 | ND | ND | 209 | 4.24 | 7.2 |
| 32 | 18 | ND | ND | ND | 13 | ND | ND | 41 | 4.2 | 7.4 |
| 33 | 60 | ND | ND | ND | 19 | ND | ND | 234 | <4 | 7.7 |
| 34 | 32 | ND | ND | ND | 17 | ND | ND | 46 | <4 | 7.0 |
| 35 | 91 | ND | ND | ND | 17 | ND | ND | 148 | <4 | 7.0 |
| 36 | 4.4 | ND | ND | ND | 3.1 | ND | ND | 17 | 4.19 | 6.5 |
| 37 | 1.0 | 0.35 | 0.95 | 1.9 | 1.3 | 7.9 | 21 | ND | ND | 6.9 |
| 38 | 0.12 | 0.32 | 0.39 | 0.19 | 0.17 | 0.21 | 0.60 | ND | <4 | 6.7 |
| 39 | 32 | ND | ND | ND | 3.5 | ND | ND | ND | 4.3 | 6.9 |
| 40 | 10 | ND | ND | ND | 4.0 | ND | ND | 7.9 | ND | 6.4 |
| 41 | 1.4 | ND | ND | ND | 1.4 | ND | ND | 1.5 | <4 | 6.6 |
| 42 | ND | ND | ND | ND | 8.7 | ND | ND | 52 | <4 | 7.1 |
| 43 | 22 | ND | ND | ND | 12.6 | ND | ND | 28 | 4.99 | 6.4 |
| 44 | 0.29 | ND | ND | ND | 0.32 | ND | ND | ND | <4 | 6.1 |
| 45 | 9.3 | ND | ND | ND | 7.4 | ND | ND | ND | <4 | 6.3 |
| 46 | ND | ND | ND | ND | ND | ND | ND | ND | <4 | 6.4 |
| 47 | 14 | ND | ND | ND | 7.8 | ND | ND | 66 | <4 | 6.4 |
| 48 | 0.37 | 1.9 | 0.38 | 0.35 | 0.32 | 0.35 | 0.85 | ND | <4 | 6.4 |
| 49 | 12 | ND | ND | ND | 1.0 | ND | ND | 3.5 | <4 | 6.3 |
| 50 | 1.4 | ND | ND | ND | 0.83 | ND | ND | 2.8 | <4 | 6.9 |
| 51 | 2.8 | ND | ND | ND | 0.89 | ND | ND | 2.1 | ND | 6.2 |
| 52 | 4.2 | 2.9 | 3.5 | 3.0 | 3.4 | 4.3 | ND | ND | <5 | 6.1 |
| 53 | ND | ND | ND | ND | ND | ND | ND | ND | 4.05 | 6.0 |
| 54 | 1.6 | 0.40 | 0.42 | 0.46 | 0.42 | 1.7 | ND | ND | <4 | 5.8 |
| 56 | 0.28 | 0.66 | 0.43 | 0.18 | 0.18 | 0.34 | 0.83 | ND | <4 | 5.7 |
| 57 | 0.37 | 0.30 | 0.31 | 0.34 | 0.32 | 0.30 | 2.0 | ND | <4 | 5.7 |
| 58 | 1.0 | 1.0 | 1.0 | 0.32 | 0.37 | 1.1 | 1.1 | ND | <4 | 5.6 |
| 59 | 1.5 | ND | ND | ND | 0.31 | ND | ND | 0.39 | <4 | 5.3 |
| 64 | 4.3 | ND | ND | ND | 1.5 | ND | ND | 13 | <4 | 7.6 |

ND indicates not determined

Bioavailability:

Caco-2 Permeability Assay for Intestinal Absorption

The permeability of different compounds is evaluated according to a Caco-2 test protocol as described by Augustijns et al. (Augustijns et al. (1998). *Int. J. of Pharm*, 166, 45-54) whereby, Caco-2 cells at cell passage number between 32 and 45 are grown in 24-well transwell cell culture plates for 21 to 25 days. The integrity of the cell monolayer is checked by measuring the transepithelial electrical resistance (TEER). The test is performed at pH 7.4 and at 100 μM donor compound concentration.

Aqueous Solubility at Different pH Levels

The equilibrium solubility in simulated gastrointestinal solutions under thermodynamic conditions is a good measure for the solubility profile of the compound in the stomach and the different parts of the intestine. Simulated gastric fluid (SGF) (without pepsin) is set at pH of 1.5. Simulated intestinal fluids (SIF) (without bile salts) are set at pH 5, pH 6.5, pH 7 and pH 7.5. The experimental protocol uses 96-well flat-bottom microplates in which 1 mg of compound is added per well (stock solution in methanol) and evaporated to dryness. The compounds are resolubilized in SGF and SIF and incubated overnight on a horizontal shaking device at 37° C. After filtration, the compound concentrations are determined by UV-spectrophotometry.

Oral Availability in the Rat

The compounds are formulated as a 20 mg/ml solution or suspension in DMSO, PEG400 or cyclodextin 40% in water. For most experiments in the rat (male and female rats), three dosing groups are formed: 1/single intraperitoneal (IP) dose at 20 mg/kg using DMSO formulation; 2/single oral dose at 20 mg/kg using PEG400 formulation and 3/single oral dose at 20 mg/kg using PEG400 formulation. Blood is sampled at regular time intervals after dosing and drug concentrations in the serum are determined using a LC-MS bioanalytical method. Serum concentrations are expressed in ng/mg. Serum concentration at 30 minutes (30') and at 3 hours (180') can be determined as these values reflect the extent of absorption (30') and the speed of elimination (180'). The rat serum concentration at 30 min and 180 min following IP administration of 20 mg/kg of compound 18 are 2012 ng/ml and 190 ng/ml respectively. The rat serum concentration at 30 min and 180 min following oral administration of 20 mg/kg as a DMSO formulation of compound 18 are 148 ng/ml and 44 ng/ml respectively; whereas in PEG400 said concentrations are respectively 475 ng/ml and 63 ng/ml.

Boosting the Systemic Bioavailability

With the described type of compounds (protease-inhibitors), it is known that inhibition of the metabolic degradation processes can markedly increase the systemic availability by reducing the first-pass metabolism in the liver and the metabolic clearance from the plasma. This 'boosting' principle can be applied in a clinical setting to the pharmacological action of the drug. This principle can be also explored both in the rat or the dog by simultaneous administration of a compound that inhibits the Cyt-p45O metabolic enzymes. Known blockers are for example ritonavir and ketoconazole. Dosing a single oral dose of ritonvir at 5 mg/kg in the rat and the dog may result in an increase of the systemic availability.

Protein Binding Analyses:

Human serum proteins like albumin (HSA) or alpha-1 acid glycoprotein (AAG) are known to bind many drugs, resulting in a possible decrease in the effectiveness of those compounds. In order to determine whether the present compounds would be adversely effected by this binding, the anti-HIV activity of the compounds was measured in the presence of human serum, thus evaluating the effect of the binding of the protease inhibitors to those proteins.

Film-Coated Tablets

Preparation of Tablet Core

A mixture of 100 g of active ingredient, in casu a compound of formula (I), 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each comprising 10 mg of the active ingredient.

Coating

To a solution of 10 g methylcellulose in 75 ml of denaturated ethanol there was added a solution of 5 g of ethylcellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

The invention claimed is:

1. A compound having the formula

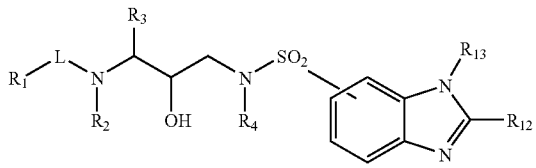

or N-oxide, salt, stereoisomeric form, racemic mixture, or ester thereof, wherein $R_1$ is a bicyclic heterocycle comprising at least 7 atoms, of which at least one is O;

L is —O—C(=O)—, —C(=O)—, —CH$_2$—O—C(=O)— or —O—CH$_2$—C(=O)—;

$R_2$ is —H;

$R_3$ is $C_{1-4}$ alkylphenyl;

$R_4$ is $C_{1-4}$ alkyl;

$R_{12}$ is —H; —NH$_2$—N($R_5$)(A$R_6$), —C$_{1-6}$alkyl or C$_{1-6}$alkyl —W—R$_{14}$, wherein said C$_{1-6}$alkyl is optionally substituted with hydroxy or amino wherein said amino is optionally mono- or di-substituted with C$_{1-4}$alkyl;

A is C$_{1-6}$alkanediyl or —C(=O)—;

$R_5$ is hydrogen;

$R_6$ is C$_{1-6}$alkyloxy, Het$^1$, amino; and in case -A- is other than C$_{1-6}$ alkanediyl then $R_6$ may also be C$_{1-6}$alkyl, Het$^1$C$_{1-4}$alkyl or aminoC$_{1-4}$alkyl; whereby each of the amino groups may optionally be substituted;

W is oxycarbonyloxy;

$R_{14}$ is Het$^1$;

$R_{13}$ is H, C$_{1-4}$alkyl, C$_{1-4}$ alkylaryl, C$_{1-4}$alkylHet$^1$ or C$_{1-4}$ alkylHet$^2$;

Het$^1$ is a saturated or partially unsaturated monocyclic, bicyclic or tricyclic heterocycle having 5 to 10 ring members, which contains one or more heteroatom ring members selected from nitrogen, oxygen or sulphur and which is optionally substituted on one or more carbon atoms by C$_{1-6}$alkyl, C$_{1-6}$alkyloxy, aminoC$_{1-6}$alkyl, halogen, hydroxy, oxo, amino, mono- or disubstituted amino, aminoalkyl, mono- or disubstituted aminoalkyl, nitro, cyano, haloC$_{1-6}$alkyl, carboxyl, C$_{1-6}$alkoxycarbonyl, C$_{3-7}$cycloalkyl, aminocarbonyl, mono- or disubstituted aminocarbonyl, methylthio, methylsulfonyl, or phenyl; and Het$^2$ is an aromatic monocyclic, bicyclic or tricyclic heterocycle having 5 to 10 ring members, which contains one or more heteroatom ring members selected from nitrogen, oxygen or sulphur and which is optionally substituted on one or more carbon atoms by $C_{1-6}$alkyl, $C_{1-6}$alkyloxy, amino$C_{1-6}$alkyl, halogen, hydroxy, amino, mono- or disubstituted amino, nitro, cyano, halo$C_{1-6}$alkyl, carboxyl, $C_{1-6}$alkoxycarbonyl, $C_{3-7}$cycloalkyl, aminocarbonyl, mono- or disubstituted aminocarbonyl, methylthio, methylsulfonyl, or phenyl.

2. A compound according to claim 1 wherein $R_1$ is a bicyclic heterocycle comprising at least 7 atoms, of which at least one is O;

L is —O—C(=O)—, —C(=O)—, —CH$_2$—O—C(=O)— or —O—CH$_2$—C(=O)—;

$R_2$ is —H;

$R_3$ is $C_{1-4}$ alkylphenyl;

$R_4$ is $C_{1-4}$ alkyl;

$R_{12}$ is H;

$R_{13}$ is $C_{1-4}$ alkylaryl, $C_{1-4}$ alkylHet$^1$, or $C_{1-4}$ alkylHet$^2$.

3. A compound according to claim 2 wherein L is —O—C(=O)—, $R_3$ is phenylmethyl and $R_4$ is 2-methylpropyl.

4. A pharmaceutical composition, comprising an effective amount of a compound as claimed in claim 1 and a pharmaceutically tolerable excipient.

5. A composition comprising (a) a compound of formula (I) as claimed in claim 1 and, (b) an antiretroviral agent for simultaneous, separate or sequential use.

* * * * *